United States Patent [19]

Kunisch et al.

[11] Patent Number: 5,622,916
[45] Date of Patent: *Apr. 22, 1997

[54] SUBSTITUTED 2-CYLCOHEXEN-1-YL-AMINE FUNGICIDAL AND HERBICIDAL AGENTS

[75] Inventors: Franz Kunisch, Odenthal-Gloebusch; Peter Babczinski, Wuppertal; Dieter Arlt, Cologne; Hans-Joachim Santel, Leverkusen; Robert R. Schmidt, Bergisch Gladbach; Wilhelm Brandes, Leichlingen; Harry Strang, Duesseldorf, all of Germany

[73] Assignee: Bayer Aktiengesellschaft, Leverkusen, Germany

[ * ] Notice: The term of this patent shall not extend beyond the expiration date of Pat. No. 5,270,340.

[21] Appl. No.: 121,671

[22] Filed: Sep. 15, 1993

Related U.S. Application Data

[62] Division of Ser. No. 762,807, Sep. 20, 1991, Pat. No. 5,270,340, which is a continuation of Ser. No. 452,460, Dec. 15, 1989, abandoned.

[30] Foreign Application Priority Data

Dec. 27, 1988 [DE] Germany ............................ 38 43 978.6
Aug. 17, 1989 [DE] Germany ............................ 39 27 115.3

[51] Int. Cl.$^6$ .......................... A01N 33/04; A01N 37/08; A01N 37/18; A01N 43/80
[52] U.S. Cl. .......................... 504/269; 504/307; 504/315; 504/319; 504/320; 504/322; 504/326; 504/334; 504/336; 514/373; 514/513; 514/529; 514/538; 514/561; 514/567; 514/613; 514/619; 514/579; 514/646; 514/647; 548/207; 558/250; 560/48; 560/125; 562/457; 562/507; 564/163; 564/188; 564/191; 564/305; 564/307; 564/462
[58] Field of Search .............................. 548/207; 560/48, 560/125; 562/457, 507; 564/191, 305, 307, 462; 514/373, 529, 538, 561, 567, 613, 646, 647; 504/269, 315, 319, 320, 322, 334, 326, 336

[56] References Cited

U.S. PATENT DOCUMENTS

| | | | |
|---|---|---|---|
| 2,512,293 | 6/1950 | Zortty et al. | 260/296 |
| 2,553,770 | 5/1951 | Killtesin et al. | 167/33 |
| 3,553,331 | 1/1971 | Paulschock | 424/325 |
| 3,692,913 | 9/1972 | Taub et al. | 424/325 |
| 4,407,671 | 10/1983 | Flint | 71/113 |
| 4,582,618 | 4/1986 | Davis et al. | 252/32.7 |
| 4,709,052 | 11/1987 | Tomioka et al. | 548/548 |
| 4,775,411 | 10/1988 | Knudsen | 71/121 |
| 5,032,616 | 7/1991 | Sauter et al. | 514/579 |
| 5,270,340 | 12/1993 | Kunisch et al. | 514/538 |

FOREIGN PATENT DOCUMENTS

| | | |
|---|---|---|
| 0113028 | 7/1984 | European Pat. Off. . |
| 0128006 | 12/1984 | European Pat. Off. . |

OTHER PUBLICATIONS

Journal of Medicinal Chemistry. 1986; vol. 29, No. 1; pp. 1–8; Stereoselective Syntheses of the trans–Decahydroquinoline–5–carboxylic Acid Epimers. Diastereomeric Zwitterionic Probes of γ-Aminobutyric Acid Related Biological Properties in Vitro and in Vivo; Donald T. Witiak et al.

Stephen P. Singer et al., J. Org Chem, vol. 43, No. 7,1978 pp. 1448–1455.

J. Am. Chem. Soc. 1981, vol. 103, pp. 2816–2822; Diels–Alder Reactions of 1–(Acylamino)–1,3–dines; Larry E. Overman et al.

J. Med. Chem 1981, vol. 24 pp. 788–794; Epimeric cis–Decahydroquinoline–5–carboxylic Acids[1] Effects on γ-Aminobutyric Acid Uptake and Receptor Binding in Vitro; Donald T. Witiak et al.

American Chemical Society 1983, 105, pp. 5373–5379; Importance of Allylic Interactions and Stereoelectronic Effects in Dictating the Steric Course of the Reaction of Iminium Ions with Nucleophiles. An Efficient Total Synthesis of (±)–Gephyrotoxin[1]; Larry E. Overman et al.

Journal of the American Chemical Society pp. 3182–3189; Diels–Alder Reactions between trans–1–N–Acylamino–1, 3–dienes and Methyl Acrylate. A Correlation between Diene Photoelectron Ionization Potentials and Reactivity, Stereoselectivity, and Regioselectivity; Larry E. Overman et al. (1978).

The Journal of Organic Chemistry; vol. 44, No. 20; Sep. 28, 1979; An Approach to Primary Allylic Amines via Transition–Metal–Catalyzed Reactions.

Total synthesis of (±)–Gabaculine; Barry M. Trost et al pp. 3451–3457.

Tetrahedron Letters, vol. 25, No. 21 pp. 2183–2186, 1984; Horner–Wadsworth Emmons Reaction: Use of Lithium Chloride and An Amide for Base–Sensitive Compounds; Mary A. Blanchette et al.

J. Org. Chem 1981, vol. 46, pp. 2833–2835; Short Total Synthesis of (±)–Perhydrogephyrotoxin; Francoise Sauriol-Lord, et al.

(List continued on next page.)

Primary Examiner—Richard L. Raymond
Attorney, Agent, or Firm—Sprung Horn Kramer & Woods

[57] ABSTRACT

A method of combating pests which comprises applying to such pests or to a pest habitat a pesticidally effective amount of a substituted 2-cyclohexen-1-yl-amine derivative of the formula

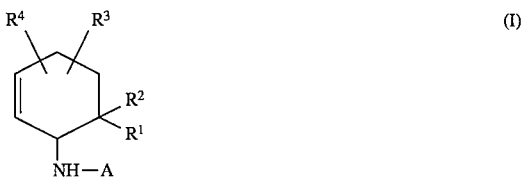

and addition products thereof with acids and metal salts. Most of the compounds are new.

7 Claims, No Drawings

OTHER PUBLICATIONS

American Chemical Society,; Synthetic Applications of N–Acylamino–1,3–dienes. An Efficient Stereospecific Total Synthesis of dl–Pumiliotoxin C, and a General Entry to cis–Decahydroquinoline Alkaloids; Larry E. Overman et al; pp. 5179–5185 (1987) vol. 100.

Chemical Abstracts vol. 117 20486(a) (1992).

STN International (Beilstein File Search BRN 3240928(1991).

SUBSTITUTED 2-CYLCOHEXEN-1-YL-AMINE FUNGICIDAL AND HERBICIDAL AGENTS

This is a division of application Ser. No. 07/762,807, filed Sep. 20, 1991, now U.S. Pat. No. 5,270,340, which is a continuation application of Ser. No. 07/452,460, filed Dec. 15, 1989, now abandoned.

The present invention relates to the use of substituted 2-cyclohexen-1-yl-amine derivatives, some of which are known, in pesticides, in particular as fungicides and herbicides, and to new substituted 2-cyclo-hexen-1-yl-amine derivatives and several processes for their preparation.

It is already known that certain tetrahydrophthalimides, such as, for example, cis-N-[(trichloromethyl)thio]-4-cyclohexene-1,2-dicarboimide, have fungicidal properties (cf., for example, Science, (Washington) 115, 84 (1952); U.S. Pat. No. 2,553,770).

However, the action of these compounds is not always entirely satisfactory in all fields of application, in particular when low application rates and application concentrations are used.

Furthermore, it is already known that 2-cycloalkenylamine derivatives and their salts, such as, for example, N-2-cyclohexen-1-yl-2,2-dimethyl-propionamide, have fungicidal properties (cf., for example, EP-OS (European Published Specification) 0,128,006).

In addition, N-benzyl-2-cyclohexen-1-yl-amine derivatives, such as, for example, N-4-methylbenzyl-2-cyclohexenylamine, have been described as intermediates for the preparation of substituted benzylcycloalkenylurea derivatives (cf. EP-OS (European Published Specification) 0,113,028).

Moreover, substituted 2-cyclohexen-1-yl-amine derivatives, such as, for example, 6-carbomethoxy-2-cyclohexan-1-yl-amine, are known as additives for lubricating oils (cf. U.S. Pat. No. 4,582,618).

Substituted 2-cyclohexen-1-yl-amine derivatives, such as, for example, 5-carbomethoxy-2-cyclohexen-1-yl-(4,4'-dimethoxybenzhydrylamine), are also described as intermediates for the synthesis of the natural substance (±)-gabaculin (cf. J. Org. Chem. 44, 3451-3457, 1979).

In addition, the Dieis-Alder reaction of various N-acylamino-1,3-butadienes with methyl acrylate to give the corresponding N-acylamino-2-cyclohexene derivatives, such as, for example, 6-carbomethoxy-2-cyclohexen-1-yl ethyl carbamate, is quantitatively investigated (cf. J. Am. Chem. Soc., 100, 3182-9, 1978).

Furthermore, the synthesis of a plurality of 2-cyclohexen-1-yl-amine derivatives has been described (cf. J. Med. Chem., 29, 1-8, 1986; J. Med. Chem., 24, 788-94, 1981, J. Am. Chem. Soc., 103, 2816-22, 1981; J. Am. Chem. Soc., 100, 3182-9, 1978; J. Am. Chem. Soc., 100, 5179-85, 1978 and Tetrahedron Lett., 25, 2183-6, 1984, J. Org. Chem., 46, 2833-5, 1981, J. Am. Chem. Soc., 105, 5373-9; 1983); however, nothing is known about their activity in the field of plant protection.

It has now been found that the substituted 2-cyclohexen-1-yl-amine derivatives, some of which are known, of the formula (I)

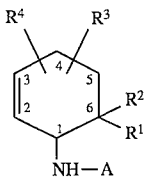

in which

R¹ represents hydrogen, alkyl or halogen,

R² represents formyl, hydroxyalkyl, cyano or nitro, or represents one of the radicals —NHR⁵, —NR⁶R⁷,

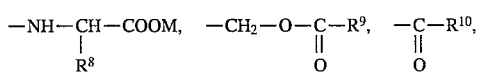

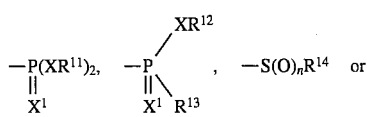

—CH=CH—R¹⁵,

R³ and R⁴ are identical or different and in each case represent hydrogen, alkyl, alkenyl, alkinyl, alkoxy, alkenyloxyor alkinyloxy, or represent unsubstituted or substituted aryl, or represent unsubstituted or substituted aralkyl, or represent unsubstituted or substituted heteroaryl, or represent unsubstituted or substituted heterocyclylalkyl, alkoxyalkyloxy or halogen, or represent one of the radicals —NH—R⁵, —NR⁶R⁷ or —S(O)ₙ—R¹⁴, or R² and R³ together represent one of the radicals

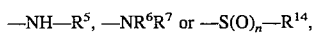

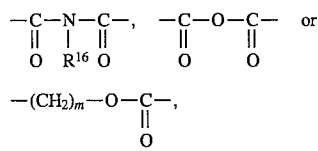

which are bridged via the 6- and 5-positions, or

R³ and R⁴ together represent an alkyl chain which has 3 or 4 carbon atoms and which is linked via the 4- and 3-positions, R⁵ represents hydrogen, alkyl or unsubstituted or substituted aryl, R⁶ represents alkyl or unsubstituted or substituted aryl, R⁷ represents alkyl or unsubstituted or substituted aryl, R⁸ represents hydrogen, alkyl, unsubstituted or substituted aryl or unsubstituted or substituted aralkyl, R⁹ represents alkyl or alkoxy, R¹⁰ represents hydroxyl, hydroxyalkyloxy, halogenalkyloxy, alkoxy, alkoxyalkyloxy, unsubstituted or substituted cycloalkyloxy, unsubstituted or substituted aralkyloxy, unsubstituted or substituted aryloxy, unsubstituted or substituted aralkyl, alkylthio or unsubstituted or substituted arylthio, or represents a group —OM, —NHR⁵, —NR⁶R⁷ or

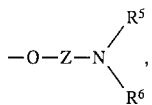

$R^{11}$ represents hydrogen or alkyl, $R^{12}$ represents hydrogen or alkyl, $R^{13}$ represents alkyl, $R^{14}$ represents alkyl, alkoxy or unsubstituted or substituted aryl, or represents the group —OM, $R^{15}$ represents formyl or cyano, or represents the group

$R^{16}$ represents hydrogen, alkyl or unsubstituted or substituted aryl,

M represents hydrogen or represents an equivalent of a corresponding alkali metal cation, alkaline earth metal cation or ammonium cation, n represents a number 0, 1 or 2, X and $X^1$ are identical or different and represent oxygen or sulphur, m represents a number 1 or 2, A represents hydrogen or an amino-protecting group, and Z represents a non-branched or branched alkyl chain, and their acid addition salts and metal salt complexes show powerful biological properties.

The compounds of the formula (I) can be present as geometric isomers (E/Z isomers) or mixtures of isomers of varying composition. The invention extends to the use of the pure isomers as well as the mixtures of isomers.

In addition, the compounds of the formula (I) contain 1 to 4 chiral centers and can therefore be present in various mixtures of enantiomers and diastereomers, which, if appropriate, can be separated in a customary manner. The invention likewise claims the use of the pure enantiomers and diastereomers as well as that of the mixtures.

For reasons of simplicity, the following will always refer to the use of compounds of the formula (I) even though there will be meant the pure compounds as well as the mixtures of varying proportions of isomeric, enantiomeric and diastereomeric compounds.

Surprisingly, the substituted 2-cyclohexen-1-yl-amine derivatives of the formula (I), some of which are known, and their acid addition salts and metal salt complexes show better fungicidal properties when applied at appropriate concentrations than cis-N-[(trichloromethyl)-thio]-4-cyclohexene-1,2-dicarboimide, which is known from the prior art and an active compound of a similar constitution and of the same type of action. The substituted 2-cyclohexen-1-yl-amine derivatives of the formula (I), some of which are known, additionally also show very good herbicidal properties when applied at appropriate concentrations.

Formula (I) provides a general definition of the substituted 2-cyclohexen-1-yl-amine derivatives to be used according to the invention.

Unless defined otherwise, the radicals in the general formulae have the following meanings:

Alkyl—straight-chain or branched alkyl having 1 to 8, preferably 1 to 6, in particular 1 to 4, carbon atoms. Examples which may preferably be mentioned are optionally substituted methyl, ethyl, n.- and i.-propyl, n-, i-, s- and t-butyl.

Alkenyl and the alkenyl moiety of optionally substituted alkenyloxy—straight-chain or branched alkenyl having 2 to 8, preferably 2 to 6, in particular 2 to 4, carbon atoms. Examples which may preferably be mentioned are optionally substituted ethenyl, 1-propenyl, 2-propenyl and 3-butenyl.

Alkinyl and the alkinyl moiety of optionally substituted alkinyloxy—straight-chain or branched alkinyl having 2 to 8, preferably 2 to 6, in particular 2 to 4, carbon atoms. Examples which may preferably be mentioned are optionally substituted ethinyl, 1-propinyl, 2-propinyl and 3-butinyl.

Alkoxy—substituted or unsubstituted straight-chain or branched alkoxy having 1 to 8, preferably 1 to 6, in particular 1 to 4, carbon atoms. Examples which may preferably be mentioned are optionally substituted methoxy, ethoxy, n.- and i.-propoxy and n-, i-, s- and t-butoxy.

Aryl—preferably unsubstituted or substituted phenyl or naphthyl, in particular phenyl.

Aralkyl and aralkoxy—unsubstituted aralkyl or aralkyl and aralkoxy, respectively, which is substituted in the aryl moiety and/or alkyl moiety, preferably having 6 or 10, in particular 6, carbon atoms in the aryl moiety (preferably phenyl or naphthyl, in particular phenyl) and preferably having 1 to 8, in particular 1 to 6, carbon atoms in the alkyl moiety, it being possible for the alkyl moiety to be straight-chain or branched. Examples which may preferably be mentioned are optionally substituted benzyl and phenylethyl as well as benzyloxy and phenylethyloxy respectively.

Unsubstituted or substituted heterocyclic radicals in the general formulae denote heteroparaffinic, heteroaromatic and heteroolefinic 5–6-membered rings, preferably having 1 to 3, in particular 1 or 2, identical or different hetero atoms. Hetero atoms are oxygen, sulphur or nitrogen. Examples which may preferably be mentioned are pyrrolidinyl, piperidinyl, furyl, thienyl, pyrazolyl, imidazolyl, 1,2,3- and 1,2,4-triazolyl, oxazolyl, isoxazolyl, thiazolyl, isothiazolyl, 1,3,4- and 1,2,4-oxadiazolyl, azepinyl, pyrrolyl, isopyrrolyl, pyridyl, pyridazinyl, pyrimidinyl, pyrazinyl and 1,2,3-, 1,2,4-, 1,2,5- and 1,3,4-thiadiazolyl.

Halogen in the general formulae preferably denotes fluorine, chlorine, bromine and iodine, in particular fluorine, chlorine and bromine, and particularly preferably fluorine and chlorine.

The optionally substituted radicals of the general formulae can carry one or more, preferably 1 to 3, in particular 1 or 2, identical or different substituents. Examples of substituents which may preferably be mentioned are:

Alkyl preferably having 1 to 4, in particular 1 or 2, carbon atoms, such as methyl, ethyl, n.- and i.-propyl and n.-, i.- and t.-butyl; alkoxy preferably having 1 to 4, in particular 1 or 2, carbon atoms, such as methoxy, ethoxy, n.- and i.-propyloxy and n.-, i.-, sec.- and t.-butyloxy; alkylthio preferably having 1 to 4, in particular 1 or 2, carbon atoms, such as methylthio, ethylthio, n.- and i.-propylthio and n.-, i.-, sec.- and t.-butylthio; halogenoalkyl, halogenoalkoxy and halogenoalkylthio, preferably having 1 to 4, in particular 1 or 2, carbon atoms and preferably 1 to 9, in particular 1 to 5, halogen atoms, the halogen atoms being identical or different, and preferably being fluorine, chlorine or bromine, in particular fluorine, such as trifluoromethyl, trifluoromethoxy, and trifluoromethylthio; hydroxyl; halogen, preferably fluorine, chlorine, bromine and iodine, in particular fluorine, chlorine and bromine; cyano; nitro; amino; dialkylamino, preferably having 1 to 4, in particular 1 or 2, carbon atoms per alkyl group, such as methyl-ethyl-amino, and methyl-n.-butyl-amino; carboxyl.

Compounds of the formula (I) which are preferably used are those in which

R¹ represents hydrogen, straight-chain or branched alkyl having 1 to 6 carbon atoms, or fluorine, chlorine or bromine, R² represents formyl, straight-chain or branched hydroxyalkyl having 1 to 8 carbon atoms in the alkyl moiety, cyano or nitro, or represents one of the radicals

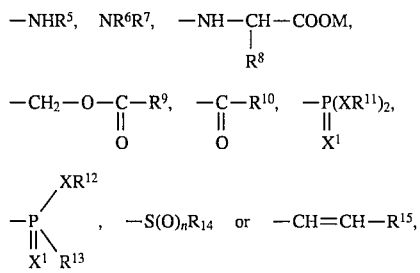

R³ and R⁴ are identical or different and in each case represent hydrogen, in each case straight-chain or branched alkyl or alkoxy having 1 to 8 carbon atoms, in each case straight-chain or branched alkenyl, alkinyl, alkenyloxy or alkinyloxy, in each case having 2 to 8 carbon atoms, or represents alkoxyalkyloxy, in each case having 1 to 8 carbon atoms in the individual alkyl moieties, or represents aryl or aralkyl, in each case having 6 to 10 carbon atoms in the aryl moiety and where appropriate 1 to 4 carbon atoms in the alkyl moiety, and in each case being unsubstituted or monosubstituted to pentasubstituted by identical or different substituents in the aryl moiety, suitable aryl substituents being: halogen, nitro, cyano, amino, $C_1$–$C_4$-alkyl, $C_1$–$C_4$-alkoxy or $C_1$–$C_1$-alkylthio, halogen-($C_1$–$C_4$—)-alkyl, halogen-($C_1$–$C_4$)-alkoxy, halogen-($C_1$–$C_4$)-alkylthio, each of which having 1 to 9 identical or different halogen atoms, and di-($C_1$–$C_4$)-alkylamino, furthermore represents a 5- or 6-membered heterocyclic ring which can contain 1 to 3 oxygen, sulphur and/or nitrogen atoms as other hetero atoms and which is unsubstituted or monosubstituted to pentasubstituted by identical or different substituents, or represents heterocyclylalkyl which is unsubstituted or monosubstituted to pentasubstituted by identical or different substituents and which comprises a 5- or 6-membered ring which may contain 1 to 3 oxygen, sulphur and/or nitrogen atoms as other hetero atoms and 1 or 2 carbon atoms in the alkyl moiety, possible substituents in the heterocycle in each case being: halogen, nitro, cyano, amino, $C_1$–$C_4$-alkyl, $C_1$–$C_1$-alkoxy, $C_1$–$C_1$-alkylthio, halogen-($C_1$–$C_4$)-alkyl, halogen-($C_1$–$C_4$)-alkoxy and halogen-($C_1$–$C_4$)-alkylthio, in each case having 1 to 9 identical or different halogen atoms, and di-($C_1$–$C_4$)-alkylamino, furthermore represent fluorine, chlorine or bromine, or represents a radical —NH—R⁵, —NR⁶R⁷ or —S(O)ₙ—R¹⁴, or R² and R³ together represent one of the radicals

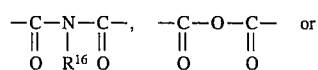

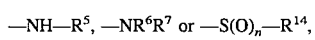

bridged via the 6- and 5-positions, or

R³ and R⁴ together represent an alkyl chain which has 3 or 4 carbon atoms and which is linked via the 4- and 3-positions, R⁵ represents hydrogen, straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned for R³, R⁶ represents straight-chain or branched alkyl having 1 to 6 carbon atoms, or represents aryl which has 6 to 10 carbon atoms and which is unsubstituted or monosubstituted to pentasubstituted by identical or different substituents, suitable aryl substituents being those aryl substituents mentioned for R³, R⁷ represents straight-chain or branched alkyl having 1 to 6 carbon atoms, or represents aryl which has 6 to 10 carbon atoms and which is unsubstituted or monosubstituted to pentasubstituted by identical or different substituents, suitable aryl substituents being those aryl substituents mentioned under R³, R⁸ represents hydrogen or straight-chain or branched alkyl having 1 to 6 carbon atoms, or represents aryl or aralkyl, in each case having 6 to 10 carbon atoms in the aryl moiety and where appropriate 1 to 4 carbon atoms in the alkyl moiety, and in each case being unsubstituted or monosubstituted to pentasubstituted in the aryl moiety by identical or different substituents, suitable aryl substituents being the aryl substituents mentioned for R³, R⁹ represents in each case straight-chain or branched alkyl or alkoxy having 1 to 6 carbon atoms, ¹⁰ represents hydroxyl, straight-chain or branched hydroxyalkyloxy with 1 to 8 carbon atoms, straight-chain or branched halogenalkyloxy with 1 to 8 carbon atoms and 1 to 17 identical or different halogen atoms, substituted cycloalkyloxy with 3 to 6 carbon atoms which is unsubstituted or mono or polysubstituted by identical or different halogen atoms, in each case straight-chain or branched alkoxy or alkylthio having 1 to 6 carbon atoms, or straight-chain or branched alkoxyalkyloxy, in each case having 1 to 6 carbon atoms in the alkoxy moiety and the alkyl moiety, or represents aryloxy, arylthio, aralkyl or aralkoxy in each case having 6 to 10 carbon atoms in the aryl moiety and where appropriate 1 to 8 carbon atoms in the alkyl moiety, and in each case being unsubstituted or monosubstituted to pentasubstituted in the aryl moiety by identical or different substituents, suitable aryl substituents being the aryl substituents mentioned for R³, or represents a group —OM, —NHR⁵, NR⁶R⁷ or

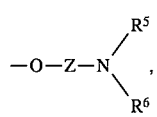

R¹¹ represents hydrogen or straight chain or branched alkyl having 1 to 6 carbon atoms, R¹² represents hydrogen or straight-chain or branched alkyl having 1 to 6 carbon atoms, $R^{13}$ represents straight-chain or branched alkyl having to 6 carbon atoms, $R^{14}$ represents in each case straight-chain or branched alkyl or alkoxy having 1 to 6 carbon atoms, or aryl which has 6 to 10 carbon atoms and which is unsubstituted or monosubstituted to pentasubstituted by identical or different substituents, suitable aryl substituents being the aryl substituents mentioned for $R^3$, or represents the group —OM, $R^{15}$ represents formyl or cyano, or represents the group

$R^{16}$ represents hydrogen, straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned above for $R^3$, m represents a number 1 or 2 and M represents hydrogen, or represents an equivalent of a corresponding alkali metal cation, alkaline earth metal cation or ammonium cation, n represents a number 0, 1 or 2, X and $X^1$ are identical or different and represent oxygen or sulphur, A represents hydrogen or an amino-protecting group and Z represents a non-branched or branched alkyl chain with 1 to 8 carbon atoms.

Other compounds to be used according to the invention are addition products of acids and those substituted 2-cyclohexen-1-yl-amine derivatives of the formula (I) in which $R^1$, $R^2$, $R^3$ and $R^4$ have the meanings which have already been mentioned in connection with the description of the substances to be used according to the invention as being preferred.

The acids which can be added on preferably include hydrohalic acids, such as, for example, hydrochloric acid and hydrobromic acid, in particular hydrochloric acid, furthermore phosphoric acid, nitric acid, monofunctional and bifunctional carboxylic acids and hydroxycarboxylic acids, such as, for example, acetic acid, trifluoroacetic acid, maleic acid, succinic acid, fumaric acid, tartaric acid, citric acid, salicylic acid, sorbic acid and lactic acid, oleic acid, stearic acid, benzoic acid which is optionally monosubstituted to polysubstituted by nitro or halogen, gluconic acid, ascorbic acid, malic acid, sulphamic acid, sulphonic acids, such as, for example, p-toluenesulphonic acid, 1,5-naphthalenedisulphonic acid and methanesulphonic acid, and imides, such as, for example, phthalimide, saccharin and thiosaccharin.

In addition, other compounds which are preferably to be used according to the invention are addition products of salts of metals of main group I, II and II and of tin, and furthermore salts of metals of sub-groups I, II, VII and VIII of the Periodic Table of the Elements and those substituted 2-cyclohexen-1-yl-amine derivatives of the formula (I) in which $R^1$, $R^2$, $R^3$ and $R^4$ have the meanings which have already been mentioned in connection with the description of the substances of the formula (I) to be used according to the invention, as being preferred for these substituents.

In this context, salts of copper, zinc, manganese, magnesium, calcium, tin, iron, cobalt and of nickel are particularly preferred. Suitable anions of these salts are those which are derived from those acids which lead to physiologically acceptable addition products. In this connection, particularly preferred acids of this type are the hydrohalic acids, such as, for example, hydrochloric acid and hydrobromic acid, and furthermore phosphoric acid, nitric acid and sulphuric acid.

Compounds of the formula (I) which are particularly preferably used are those in which $R^1$ represents hydrogen, straight-chain or branched alkyl having 1 to 4 carbon atoms, or fluorine, chlorine or bromine, $R^2$ represents formyl, straight-chain or branched hydroxyalkyl having 1 to 4 carbon atoms in the alkyl moiety, cyano or nitro, or represents one of the radicals

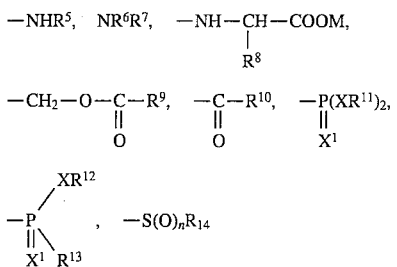

or —CH=CH—$R^{15}$, $R^3$ and $R^4$ are identical or different and in each case represent hydrogen, in each case straight-chain or branched alkyl or alkoxyhaving 1 to 6 carbon atoms, in each case straight-chain or branched alkenyl, alkinyl, alkenyloxy or alkinyloxy, in each case having 2 to 6 carbon atoms, or represents alkoxyalkyloxy, in each case having 1 to 6 carbon atoms in the individual alkyl moieties, or represents phenyl or phenylalkyl, where appropriate having 1 or 2 carbon atoms in the alkyl moiety, and in each case being unsubstituted or monosubstituted to pentasubstituted in the phenyl moiety by identical or different substituents, suitable phenyl substituents being: fluorine, chlorine, bromine, nitro, cyano, amino, $C_1$-$C_2$-alkyl, $C_1$-$C_3$-alkoxy or $C_1$-$C_2$-alkylthio, halogeno-($C_1$-$C_2$)-alkyl, halogeno-($C_1$-$C_2$)-alkoxy and halogeno-($C_1$-$C_2$)-alkylthio, in each case having 1 to 5 identical or different fluorine and/or chlorine atoms, furthermore represents a heterocyclic five- or six-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which group is unsubstituted or monosubstituted to trisubstituted by identical or different substituents and if appropriate bonded via a methylene group, suitable substituents on the heterocycle in each case being: fluorine, chlorine, bromine, nitro, cyano, amino, $C_1$-$C_2$-alkyl, $C_1$-$C_2$-alkoxy, $C_1$-$C_2$-alkylthio, halogeno-($C_1$-$C_2$)-alkyl, halogeno-($C_1$-$C_2$)-alkoxy and halogen-($C_1$-$C_2$)-alkylthio, each having 1 to 5 identical or different fluorine and/or chlorine atoms, and di-($C_1$-$C_2$)-alkylamino, furthermore represents fluorine, chlorine or bromine, or represents one of the radicals

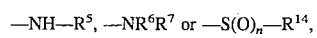

or $R^2$ and $R^3$ together represent one of the radicals

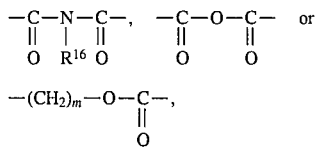

bridged via the 6- and 5-positions,
or
$R^3$ and $R^4$ together represents an alkyl chain which has 3 or 4 carbon atoms and which is linked via the 4- and 3-positions, $R^5$ represents hydrogen, straight-chain or branched alkyl having 1 to 4 carbon atoms, or phenyl which is unsubstituted or monosubstituted to pentasubstituted by identical or different substituents, suitable phenyl substituents being the phenyl substituents mentioned for $R^3$, $R^6$ represents straight-chain or branched alkyl having 1 to 4 carbon atoms, or phenyl which is unsubstituted or monosubstituted to pentasubstituted by identical or different substituents, suitable phenyl substituent being those phenyl substituents mentioned for $R^3$, $R^7$ represents straight-chain or branched alkyl having 1 to 4 carbon atoms, or phenyl which is unsubstituted or monosubstituted to pentasubstituted by identical or different substituents, suitable phenyl substituents being those phenyl substituents mentioned for $R^3$, $R^8$ represents hydrogen or straight-chain or branched alkyl having 1 to 4 carbon atoms, or represents phenyl of phenylalkyl, where appropriate having 1 or 2 carbon atoms in the alkyl moiety, and in each case being unsubstituted or monosubstituted to pentasubstituted in the phenyl moiety by identical or different substituents, suitable phenyl substituents being the phenyl substituents mentioned for $R^3$, $R^9$ represents in each case straight-chain or branched alkyl or alkoxy having 1 to 4 carbon atoms, $R^{10}$ represents hydroxyl, straight-chain or branched hydroxyalkyloxy with 1 to 6 carbon atoms, straight-chain or branched halogenalkyloxy with 1 to 6 carbon atoms and 1 to 13 identical or different halogen atoms, substituted cycloalkyloxy with 3 to 6 carbon atoms which is unsubstituted or mono or trisubstituted by identical or different fluoro, chloro or bromo atoms, in each case straight-chain or branched alkoxy or alkylthio having 1 to 4 carbon atoms, or straight-chain or branched alkoxyalkyloxy, in each case having 1 to 4 carbon atoms in the alkoxy moiety or alkyl moiety, or phenyloxy, phenylthio, phenylalkyl or phenylalkyloxy, where appropriate in each case having 1 to 6 carbon atoms in the alkyl moiety and in each case being unsubstituted or monosubstituted to pentasubstituted in the phenyl moiety by identical or different substituents, suitable phenyl substituents being those phenyl substituents mentioned for $R^3$, or represents a group —OM, —NHR$^5$, —NR$^6$R$^7$ or

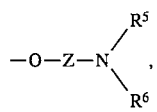

$R^{11}$ represents hydrogen or straight-chain or branched alkyl having 1 to 4 carbon atoms, $R^{12}$ represents hydrogen or straight-chain or branched alkyl having 1 to 4 carbon atoms, $R^{13}$ represents straight-chain or branched alkyl having 1 to 4 carbon atoms, $R^{14}$ represents in each case straight-chain or branched alkyl or alkoxy having 1 to 4 carbon atoms, or phenyl which is unsubstituted or monosubstituted to pentasubstituted by identical or different substituents, suitable phenyl substituents being the phenyl substituents mentioned for $R^3$, or represents the group —OM, $R^{15}$ represents formyl or cyano, or represents the group

$R^{18}$ represents hydrogen, straight-chain or branched alkyl having 1 to 4 carbon atoms, or phenyl which is unsubstituted or monosubstituted to pentasubstituted by identical or different substituents, suitable phenyl substituents being the phenyl substituents mentioned above for $R^3$, m represents a number 1 or 2 and M represents hydrogen, or represents an equivalent of a corresponding sodium cation, potassium cation or ammonium cation, n represents a number 0, 1 or 2, X and $X^1$ are identical or different and represent oxygen or sulphur, A represents hydrogen or an amino-protecting group and Z represents a non-branched or branched alkyl chain with 1 to 6 carbon atoms.

The term "amino-protecting group" is generally known and relates to groups which are suitable for protecting (for blocking) an amino group from chemical reactions, but which are readily detachable after the desired reaction has been carried out on other sites of the molecule. Representative of such groups are, in particular, unsubstituted or substituted acyl, aryl—for example DNP (2,4-dinitrophenyl), aralkoxymethyl—for example BOM (N-(benzyloxy)methyl), or aralkyl groups (for example benzyl, 4-nitrobenzyl, triphenylmethyl). Incidentally, since the amino-protecting groups are removed after the desired reaction (or sequence of reactions), their nature and size is not critical; however, those having 1–20, in particular 1–8, carbon atoms are preferred. In connection with the present invention, the term "acyl group" is taken to mean acyl groups in the broadest sense. It comprises acyl groups derived from aliphatic, araliphatic, aromatic or heterocyclic carboxylic acids or sulphonic acids, and in particular alkoxycarbonyl, aryloxycarbonyl and especially aralkoxycarbonyl groups. Examples of acyl groups of this type are alkanoyl, such as acetyl, propionyl, butyryl; aralkanoyl such as phenylacetyl; aroyl such as benzoyl or toluyl; aryloxyalkanoyl, such as POA (phenoxyacetyl); alkoxycarbonyl, such as methoxycarbonyl, ethoxycarbonyl, 2,2,2-trichloroethoxycarbonyl, BOC (tert.-butoxycarbonyl), 2-iodoethoxycarbonyl; aralkyloxycarbonyl, such as CBZ ("carbobenzoxy") and 4-methoxybenzyloxycarbonyl. Preferred amino-protecting groups are benzyl, acetyl, methoxycarbonyl, allyloxycarbonyl, trichloroethyloxycarbonyl, (±)-menthyloxycarbonyl, tert-butoxycarbonyl and benzyloxycarbonyl.

The application furthermore relates to new substituted 2-cyclohexen-1-yl-amine derivatives of the formula (Ia)

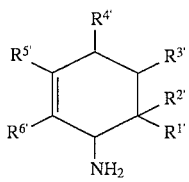 (Ia)

in which
- $R^{1'}$ represents hydrogen, alkyl or halogen,
- $R^{2'}$ represents formyl, hydroxyalkyl, cyano or nitro, or represents one of the radicals

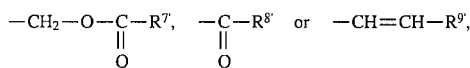

- $R^{3'}$, $R^{4'}$, $R^{5'}$ and $R^{6'}$ are identical or different and in each case represent hydrogen, alkyl, alkenyl, alkinyl, alkoxy, alkenyloxy and alkinyloxy; or represent unsubstituted or substituted aryl, or represent unsubstituted or substituted aralkyl, or represent unsubstituted or substituted heteroaryl, or represent unsubstituted or substituted heterocyclylalkyl, or represent alkoxyalkyloxy, or represent halogen, where at least two of the radicals $R^{3'}$, $R^{4'}$, $R^{5'}$ or $R^{6'}$ represent hydrogen,
- $R^{7'}$ represents alkyl or alkoxy,
- $R^{8'}$ represents hydroxyl, hydroxyalkyloxy, halogenalkyloxy, alkoxy or alkoxyalkyloxy, unsubstituted or substituted cycloalkyloxy, unsubstituted or substituted aralkyloxy, unsubstituted or substituted aryloxy, unsubstituted or substituted aralkyl, alkylthio or unsubstituted or substituted arylthio, or represents a group

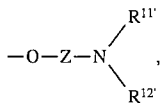

- $R^{9'}$ represents formyl or cyano, or represents the group

- $R^{10'}$ represents hydrogen, alkyl or unsubstituted or substituted aryl,
- $R^{11'}$ and $R^{12'}$ are identical or different and in each case represent alkyl or unsubstituted or substituted aryl, and
- M represents hydrogen, or represents an equivalent of a corresponding alkali metal cation, alkaline earth metal cation or ammonium cation and
- Z represents a non-branched or branched alkyl chain or
- $R^{2'}$ and $R^{3'}$ together represent one of the radicals

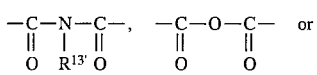

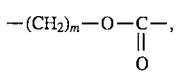

bridged via the 6- and 5-positions,
where
- $R^{13'}$ represents hydrogen, alkyl or unsubstituted or substituted aryl and
- m represents a number 1 or 2, or
- $R^{4'}$ and $R^{5'}$ together represent an alkyl chain which has 3 or 4 carbon atoms and which is linked via the 4- and 3-positions, and their acid addition salts and metal salt complexes.

Formula (Ia) provides a general definition of the substituted 2-cyclohexen-1-yl-amine derivatives which were hitherto unknown.

Preferred compounds of the formula (Ia) are those in which
- $R^{1'}$ represents hydrogen, straight-chain or branched alkyl having 1 to 6 carbon atoms, or fluorine, chlorine or bromine,
- $R^{2'}$ represents formyl, straight-chain or branched hydroxyalkyl having 1 to 8 carbon atoms in the alkyl moiety, cyano or nitro, or represents one of the radicals

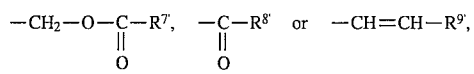

- $R^{3'}$, $R^{4'}$, $R^{5'}$ and $R^{6'}$ are identical or different and in each case represent hydrogen, in each case straight-chain or branched alkyl or alkoxy having 1 to 8 carbon atoms, in each case straight-chain or branched alkenyl, alkinyl, alkenyloxy or alkinyloxy, in each case having 2 to 8 carbon atoms, or alkoxyalkyloxy, in each case having 1 to 8 carbon atoms in the individual alkyl moieties, or represents aryl or aralkyl, having in each case 6 to 10 carbon atoms in the aryl moiety and where appropriate 1 to 4 carbon atoms in the alkyl moiety, and in each case being unsubstituted or monosubstituted to pentasubstituted in the aryl moiety by identical or different substituents, suitable aryl substituents being: halogen, nitro, cyano, amino, $C_1$–$C_4$-alkyl, $C_1$–$C_4$-alkoxy, $C_1$–$C_1$-alkylthio, halogeno-($C_1$–$C_4$)-alkyl, halogeno-($C_1$–$C_4$)-alkoxy, halogeno-($C_1$–$C_4$)-alkylthio, each having 1 to 9 identical or different halogen atoms, and di-($C_1$–$C_4$)-alkylamino, furthermore represent a heterocyclic 5- or 6-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which group is unsubstituted or monosubstituted to trisubstituted by identical or different substituents and where appropriate linked via a methylene group, suitable substituents on the heterocycle in each case being: halogen, nitro, cyano, amino, $C_1$–$C_1$-alkyl, $C_1$–$C_4$-alkoxy or $C_1$–$C_1$-alkylthio, halogeno-($C_1$–$C_4$)-alkyl, halogeno-($C_1$–$C_4$)-alkoxy or halogeno-($C_1$–$C_4$)-alkylthio, in each case having 1 to 9 identical or different halogen atoms, and di-($C_1$–$C_4$)-alkylamino, furthermore represent fluorine, chlorine or bromine, where at least two of the radicals $R^{3'}$, $R^{4'}$, $R^{5'}$ or $R^{6'}$ represent hydrogen,
- $R^{7'}$ represents in each case straight-chain or branched alkyl or alkoxy having 1 to 6 carbon atoms,
- $R^{8'}$ represents hydroxyl, straight-chain or branched hydroxyalkyloxy with 1 to 8 carbon atoms, straight-chain or branched halogenalkyloxy with 1 to 8 carbon atoms end 1 to 17 identical or different halogen atoms, substituted cycloalkyloxy with 3 to 6 carbon atoms which is unsubstituted or mono or polysubstituted by identical or different halogen atoms, in each case straight-chain or branched alkoxy or alkylthio having 1 to 6 carbon atoms, or straight-chain or branched alkoxyalkyloxy, in each case having 1 to 6 carbon atoms in the alkoxy moiety or alkyl moiety, or aryloxy, arylthio, aralkyl or aralkyloxy, in each case having 6 to 10 carbon atoms in the aryl moiety and where appropriate 1 to 8 carbon atoms in the alkyl moiety, and in each case being unsubstituted or monosubstituted to pentasubstituted in the aryl moiety by identical or different substituents, suitable aryl substituents being the aryl substituents mentioned above, or represents a group

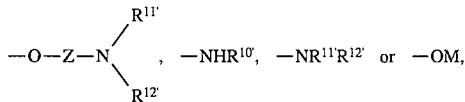

$R^{9'}$ represents formyl or cyano, or represents the group

$R^{10'}$ represents hydrogen, straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned above, $R^{11'}$ represents straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned above, $R^{12'}$ represents straight-chain or branched alkyl having 1 to 6 carbon atoms, or aryl which has 6 to 10 carbon atoms and which is unsubstituted or monosubstituted to pentasubstituted by identical or different substituents, suitable aryl substituents being the aryl substituents mentioned above, M represents hydrogen, or represents an equivalent of a corresponding alkali metal cation, alkaline earth metal cation or ammonium cation, and Z represents a non-branched OF branched alkyl chain with 1 to 8 carbon atoms, or $R^{2'}$ and $R^{3'}$ together represent one of the radicals

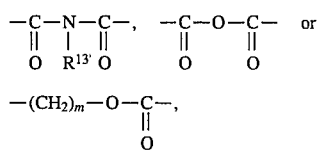

bridged via the 6- and 5-positions,
where
$R^{13'}$ represents hydrogen, straight-chain or branched alkyl having 1 to 6 carbon atoms or aryl which has 6 to 10 carbon atoms and which is unsubstituted or monosubstituted to pentasubstituted by identical or different substituents, suitable aryl substituents being the aryl substituents mentioned above, and m represents a number 1 or 2,
or $R^{4'}$ and $R^{5'}$ together represent an alkyl chain which has 3 or 4 carbon atoms and which is linked via the 4- and 3-positions.

Other preferred compounds according to the invention are addition products of acids and those substituted 2-cyclohexen-1-yl-amine derivatives of the formula (Ia) in which $R^{1'}$, $R^{2'}$, $R^{3'}$, $R^{4'}$, $R^{5'}$ and $R^{6'}$ have the abovementioned meanings.

The acids which can be added on preferably include hydrohalic acids, such as, for sxample, hydrochloric acid or hydrobromic acid, in particular hydrochloric acid, furthermore phosphoric acid, nitric acid, monofunctional and bifunctional carboxylic acids and hydroxycarboxylic acids, such as, for example, acetic acid, trifluoroacetic acid, maleic acid, succinic acid, fumaric acid, tartaric acid, citric acid, salicylic acid, sorbic acid and lactic acid, oleic acid, stearic acid, benzoic acid which is optionally monosubstituted or polysubstituted by nitre or halogen, gluconic acid, ascorbic acid, malic acid, sulphamic acid, sulphonic acids, such as, for example, p-toluenesulphonic acid, 1,5-naphthalenedisulphonic acid and methanesulphonic acid, and imides, such as, for example, phthalimide, saccharin and thiosaccharin.

In addition, other preferred compounds according to the invention are addition products of salts of metals of main groups I, II and III and of tin, and furthermore salts of metals of sub-groups I, II, VII and VIII of the Periodic Table of the Elements and those substituted 2-cyclohexen-1-yl-amine derivatives of the formula (Ia) in which $R^{1'}$, $R^{2'}$, $R^{3'}$, $R^{4'}$, $R^{5'}$ and $R^{6'}$ have the abovementioned meanings.

In this context, salts of copper, zinc, manganese, magnesium, calcium, tin, iron, cobalt and of nickel are particularly preferred. Suitable anions of these salts are those which are derived from those acids which lead to physiologically acceptable addition products. In this connection, particularly preferred acids of this type are the hydrohalic acids, such as, for example, hydrochloric acid and hydrobromic acid, and furthermore phosphoric acid, nitric acid and sulphuric acid.

Particularly preferred compounds of the formula (Ia) are those in which $R^{1'}$ represents hydrogen, straight-chain or branched alkyl having 1 to 4 carbon atoms, or fluorine, chlorine or bromine, $R^{2'}$ represents formyl, straight-chain or branched hydroxyalkyl having 1 to 4 carbon atoms in the alkyl moiety, cyano or nitro, or represents one of the radicals

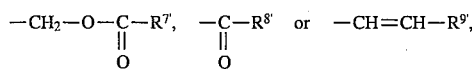

$R^{3'}$, $R^{4'}$, $R^{5'}$ and $R^{6'}$ are identical or different and in each case represent hydrogen, in each case straight-chain or branched alkyl or alkoxy having 1 to 6 carbon atoms, in each case straight-chain or branched alkenyl, alkinyl, alkenyloxy or alkinyloxy, in each case having 2 to 6 carbon atoms, or alkoxyalkyloxy, in each case having 1 to 6 carbon atoms in the individual alkyl moieties, or represent phenyl or phenylalkyl, where appropriate having 1 or 2 carbon atoms in the alkyl moiety, and in each case being unsubstituted or monosubstituted to trisubstituted in the phenyl moiety by identical or different substituents, suitable phenyl substituents being: fluorine, chlorine, bromine, nitro, cyano, amino, $C_1$–$C_2$-alkyl, $C_1$–$C_3$-alkoxy, $C_1$–$C_2$-alkylthio, halogeno-($C_1$–$C_2$)-alkyl, halogeno-($C_1$–$C_2$)-alkoxy and halogeno-($C_1$–$C_2$)-alkylthio, in each case having 1 to 5 identical or different fluorine and/or chlorine atoms, and di-($C_1$–$C_2$)-alkylamino, furthermore represent a heterocyclic five- or six-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which group is unsubstituted or monosubstituted to trisubstituted by identical or different substituents and where appropriate bonded via a methylene group, suitable substituents on the heterocycle in each case being: fluorine, chlorine, bromine, nitro, cyano, amino, $C_1$–$C_2$-alkyl, $C_1$–$C_2$-alkoxy or $C_1$–$C_2$-alkylthio, halogeno-($C_1$–$C_2$)-alkyl, halogeno-($C_1$–$C_2$)-alkoxy and halogeno-($C_1$–$C_2$)-alkylthio, in each case having 1 to 5 identical or different fluorine and/or chlorine atoms, and di-($C_1$–$C_2$)-alkylamino, furthermore represent fluorine, chlorine or bromine, where at least two of the radicals $R^{3'}$, $R^{4'}$, $R^{5'}$ and $R^{6'}$ represent hydrogen, $R^{7'}$ represents in each case straight-chain or branched alkyl or alkoxy having 1 to 4 carbon atoms, $R^{8'}$ represents hydroxyl, straight-chain or branched hydroxyalkyloxy with 1 to 6 carbon atoms, straight-chain or branched halogenalkyloxy with 1 to 6 carbon atoms and 1 to 13 identical or different halogen atoms, substituted cycloalkyloxy with 3 to 6 carbon atoms which is unsubstituted or mono or trisubstituted by identical or different fluoro, chloro or bromo atoms, in each case straight-chain or branched alkoxy or alkylthio having 1 to 4 carbon atoms, or straight-chain or branched alkoxyalkylalkoxy, in each case having 1 to 4 carbon atoms in the alkoxy moiety or alkyl moiety, or phenyloxy, phenylthio, phenylalkyl, or phenylalkyloxy, where appropriate in each case having 1 to 6 carbon atoms in the alkyl moiety, and in each case unsubstituted or monosubstituted to trisubstituted in the phenyl moiety by identical or different substituents, suitable phenyl substituents being the phenyl substituents mentioned above, or represents a group

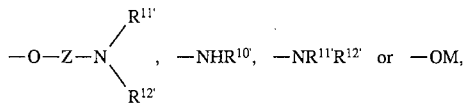

$R^{9'}$ represents formyl or cyano, or represents the group

$R^{10'}$ represents hydrogen, straight-chain or branched alkyl having 1 to 4 carbon atoms, or phenyl which is unsubstituted or monosubstituted to trisubstituted by identical or different substituents, suitable phenyl substituents being the phenyl substituents mentioned above, $R^{11'}$ represents straight-chain or branched alkyl having 1 to 4 carbon atoms, or phenyl which is unsubstituted or monosubstituted to trisubstituted by identical or different substituents, suitable phenyl substituents being the phenyl substituents mentioned above, $R^{12'}$ represents straight-chain or branched alkyl having 1 to 4 carbon atoms, or phenyl which is unsubstituted or monosubstituted to trisubstituted by identical or different substituents, suitable phenyl substituents being the phenyl substituents mentioned above, M represents hydrogen, or represents an equivalent of a corresponding alkali metal cation, alkaline earth metal cation of ammonium cation, and Z represents a non-branched or branched alkyl chain with 1 to 6 carbon atoms, $R^{2'}$ and $R^{3'}$ together represent one of the radicals

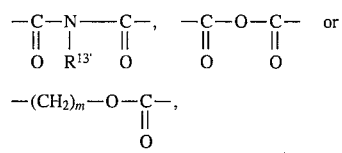

bridged via the 6- and 5-positions, $R^{13'}$ represents hydrogen, straight-chain or branched alkyl having 1 to 6 carbon atoms or phenyl which is unsubstituted or monosubstituted to trisubstituted by identical or different substituents, suitable phenyl substituents being the phenyl substituents mentioned above, and m represents a number 1 or 2, or $R^{4'}$ and $R^{5'}$ together represent an alkyl chain which has 3 or 4 carbon atoms and which is linked via the 4- and 3-positions.

In this connection, the same acid addition salts and metal salt complexes may be mentioned which have already been mentioned in the description of the preferred 2-cyclohexen-1-yl-amine derivatives, substituted according to the invention, of the formula (Ia).

The substituted 2-cyclohexen-1-yl-amine derivatives of the formula (Ia) are obtained when A) 2-cyclohexen-1-yl-carboxylic acid derivatives of the formula (II)

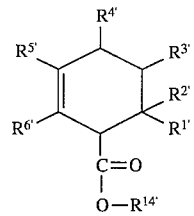

in which $R^{1'}$, $R^{2'}$, $R^{3'}$, $R^{4'}$, $R^{5'}$ and $R^{6'}$ have the abovementioned meanings and $R^{14'}$ represents hydrogen, methyl or ethyl, are treated in a generally customary manner with chloroformic acid ester, by the method of Curtius, if appropriate in the presence of a diluent, such as, for example, acetone, and in the presence of a base, such as, for example, N,N-diisopropylamine, at temperatures between −15° C. and +10° C., and adding an azide, such as, for example, sodium azide, to this reaction mixture, if appropriate in the presence of a diluent, such as, for example, water, at temperatures between −5° C. and +25° C., and hydrolyzing the isocyanate which occurs as an intermediate, of the formula (IIa)

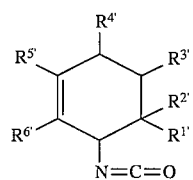

in which

R¹', R²', R³', R⁴', R⁵' and R⁶' have the abovementioned meanings,
with water, if appropriate in the presence of an acid or a base, and, if desired, converting the resulting amines into acid addition salts and metal salt complexes [cf. J. Org. Chem. 26, (1961), 3511].

In addition, the substituted 2-cyclohexen-1-yl-amine derivatives of the formula (Ia) are obtained
B) from the 2-cyclohexene derivatives of the formula (IIb)

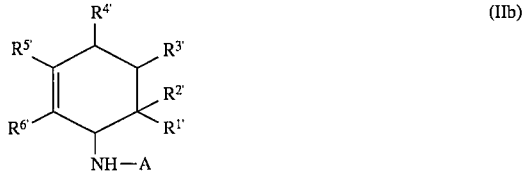

in which
R¹', R²', R³', R⁴', R⁵' and R⁶' have the abovementioned meanings and

A represents an amino-protecting group, in a known manner by customary methods, for example by solvolysis, such as hydrolysis or acidolysis, by reduction, such as, for example, by hydrogenolysis in the presence of a hydrogenation catalyst or by means of a reduction system of metal and proton-eliminating agent, where, depending on the nature of the protecting group, various types of eliminating methods (also different types) and selective elimination methods can be used, if appropriate in the presence of a suitable solvent or diluent or a mixture thereof, where, if required with cooling, at room temperature or with heating, for example in a temperature range of about −10° C. to the boiling point of the reaction medium, preferably from about −10° C. to about 150° C., the process is carried out, if required, in a sealed vessel, under pressure, under an atmosphere of inert gas and/or under anhydrous conditions, and, if desired, the resulting products are converted into acid addition salts or metal salt complexes (cf. Protective Groups in Organic Synthesis, Th. W. Greene, Wiley Interscience, 1981).

The formyl, acetyl or 2,2,2-trichloroacetyl group, which was mentioned before as, inter alia, amino-protecting group, can be eliminated for example by hydrolysis.

The hydrolysis is carried out in a manner known per se with the aid of water, it being advantageous to carry out the hydrolysis in the presence of an acid or base which assists hydrolysis, if appropriate in the presence of an inert solvent or diluent and/or with cooling or heating.

Examples of suitable acids are inorganic acids, such as mineral acids, for example sulphuric acid, phosphoric acid or hydrohalic acids, organic carboxylic acids, such as lower alkanecarboxylic acids, for example glacial acetic acid, such as optionally unsaturated dicarboxylic acids, for example oxalic, malonic, maleic or fumaric acid, or such as hydroxycarboxylic acids, for example tartaric acid or citric acid, or sulphonic acids, such as $C_1$–$C_7$-alkanesulphonic acid or optionally substituted benzenesulphonic acid, for example methanesulphonic acid or p-toluenesulphonic acid.

Examples of suitable bases are the hydroxides, hydrides, amides, alkanolates, carbonates, triphenylmethylides, di-$C_1$–$C_7$-alkylamides, amino-$C_1$–$C_7$-alkylamides or $C_1$–$C_7$-alkylsilylamides of alkali metals, or naphthaleneamines, $C_1$–$C_7$-alkylamines, basic heterocyclic compounds, ammonium hydroxides, and carbocyclic amines. Examples which may be mentioned are lithium hydroxide, sodium hydroxide, sodium hydride, sodium amide, sodium ethylate, potassium tert-butylate, potassium carbonate, lithium triphenylmethylide, lithium diisopropylamide, potassium 3-(aminopropyl)amide, potassium bis-(trimethylsilyl)-amide, dimethyl-aminonaphthalene, diethylamine or triethylamine, pyridine, benzyltrimethyl-ammoniumhydroxide, 1,5-diazabicyclo-[4.3.0]non-5-ene (DBN), and 1,8-diaza-bicyclo-[5.4.0]undec-7-ene (DBU).

Acidolysis is successfully carried out, for example using strong acids, it being advantageous to use trifluoroacetic acid or perchloric acid, but also using other strong inorganic acids, such as hydrochloric acid or sulphuric acid, strong organic carboxylic acids, such as trichloroacetic acid, or sulphonic acids, such as benzenesulphonic acid or p-toluenesulphonic acid. An additional inert solvent may be present. Preferably, organic solvents, for example carboxylic acids, such as acetic acid, ethers, such as tetrahydrofuran or dioxane, amides, such as dimethylformamide (DMF), halogenated hydrocarbons, such as dichloromethane, furthermore also alcohols, such as methanol, ethanol or isopropanol, and water, are suitable as inert solvents.

Other suitable solvents are mixtures of the abovementioned solvents. Trifluoroacetic acid is preferably used in excess without the addition of a further solvent, perchloric acid is preferably used in the form of a mixture of acetic acid and 70% strength perchloric acid in the ratio 9:1. The reaction temperatures of these solvolyses are expediently between about 0° and about 50° C., the reaction preferably being carried out between 15° and 30° C. (room temperature).

A preferred way of eliminating the BOC group is for example using 40% strength trifluoroacetic acid in methylene chloride or using about 3 to 5N hydrochloric acid in dioxane at 15°–30° C., and a preferred way of eliminating the FMOC group (9-fluorenylmethyloxycarbonyl) using an approximately 5- to 20% strength solution of dimethylamine, diethylamine or piperidine in dimethylformamide at 15°–30° C. The DNP group (2,4-dinitrophenyl) can also successfully be eliminated, for example using an approximately 3- to 10% strength solution of 2-mercaptoethanol in dimethylformamide/water at 15°–30° C. Protecting groups which can be removed by hydrogenolysis (for example BOM, CBZ or benzyl) can be eliminated, for example by treatment with hydrogen in the presence of a catalyst (for example a noble-metal catalyst, such as palladium, expediently on a support, such as carbon). Suitable solvents for this process are those mentioned above, in particular, for example, alcohols, such as methanol or ethanol, or amides, such as dimethylformamide. Hydrogenolysis is usually carried out at temperatures from about 0° to 100° C. and at a pressure from about 1 to 200 bar, preferably at 20°–30° C. and 1–10 bar. Hydrogenolysis of the CBZ group is easily carried out, for example, using 5- to 10% strength Pd-carbon in methanol at 20°–30° C.

Examples which may be mentioned of amino-protecting groups which are eliminated using a reducing system of metal and proton-eliminating agent are (4-nitro)benzyloxycarbonyl, 2-iodoethoxycarbonyl or 2,2,2-trichloroethoxycarbonyl or phenacyloxycarbonyl.

An example of the metal constituent of the metal reducing system is a non-noble metal, such as an alkali metal or alkaline earth metal, for example lithium, sodium, potassium, magnesium or calcium, or a transition metal, for example zinc, tin, iron or titanium, while possible protoneliminating agents are, for example, protonic acids of the abovementioned type, such as hydrochloric acid or acetic acid, $C_1$–$C_7$-alcohols, such as ethanol, and/or amines, or ammonia. Examples of such systems are sodium/ammonia, zinc/hydrochloric or acetic acid, or zinc/ethanol.

Furthermore, 4-nitrobenzyloxycarbonyl can be split, for example, using a dithionite, such as sodium dithionite, phenacyloxycarbonyl and 2-halogeno-$C_2$-$C_7$-alkanoyl can be split, for example, with the aid of a nucleophilic reagent, such as a thiolate, for example sodium thiophenolate, or using thiourea and base and subsequent hydrolysis, and allyl or but-2-enyl can be split with the aid of a rhodium(III) halide, such as rhodium(III) chloride.

The compounds of the formula (I) which are known may be prepared in analogy to the new compounds of the formula (Ia).

If, for example, methyl 2-carboxy-5-methylcyclohex-3-ene-carboxylate and ethyl chloroformate are used as starting substances, N,N-diisopropylethylamine is used as the base for step one, and sodium azide and water are used for step two, the course of the reaction of preparation process (A) may be represented by the following equation:

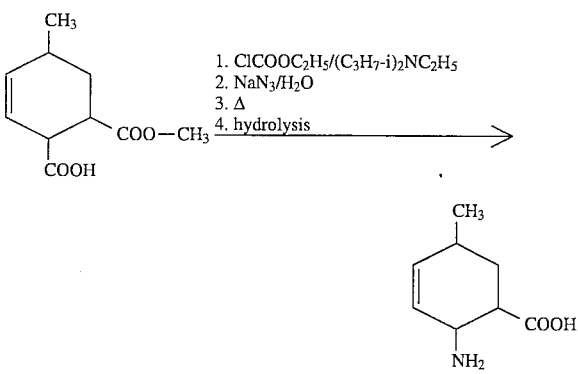

If, for example, tert-butyl 3-methyl-6-carboxy-2-cyclohexen-1-yl-carbamate and 1N hydrochloric acid are used as starting substances, the course of the reaction of preparation process (B) may be represented by the following equation:

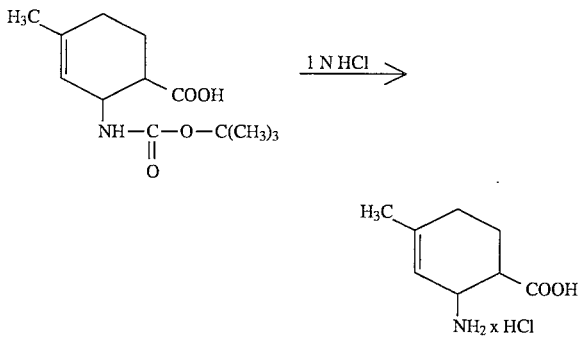

Formula (II) provides a general definition of the 2-cyclohexen-1-yl-carboxylic acid derivatives required as starting substances for carrying out preparation process (A). In this formula (II), $R^{1'}$, $R^{2'}$, $R^{3'}$, $R^{4'}$, $R^{5'}$ and $R^{6'}$ preferably, or in particular, represent those substituents which have been mentioned above in the description of the new 2-cyclohexen-1-yl-amine derivatives of the formula (Ia) as being preferred, or particularly preferred, for these radicals.

Some of the 2-cyclohexen-1-yl-carboxylic acid derivatives of the formula (II) are known and/or can be prepared by known processes in a simple, analogous manner (cf. Houben-Weyl, Methoden der Organischen Chemie [Methods of Organic Chemistry], 4th edition, E.Muller, Ed. Vol. 5/Ic, Georg Thieme Verlag, Stuttgart, 1970, 977; J. Chem. Soc. Perkin Trans. 1, 1557–62, 1981), for example by cyclizing the known dienophilic compounds which have the formula (III)

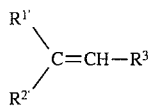 (III)

in which $R^{1'}$, $R^{2'}$ and $R^{3'}$ have the abovementioned meanings, and which are known, with the corresponding dienecarboxylic acid derivatives of the formula (IV)

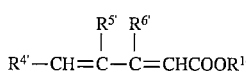 (IV)

in which $R^{4'}$, $R^{5'}$ and $R^{6'}$ have the abovementioned meanings and $R^{14'}$ represents hydrogen, methyl or ethyl, if appropriate in the presence of a diluent, if appropriate in the presence of a catalyst, if appropriate in the presence of an inert gas and if appropriate under pressure, at temperatures between –50° C. and 150° C.

Formula (III) provides a general definition of the dienophilic compounds required as starting substances for the preparation of the 2-cyclohexen-1-yl-carboxylic acid derivatives of the formula (II) and of the 2-cyclohexene derivatives of the formula (IIb). In this formula (III), $R^{1'}$, $R^{2'}$ and $R^{3'}$ represent those radicals which have already been mentioned in connection with the description of the compounds of the formula (Ia) according to the invention for these substituents.

The following may be mentioned by way of example for compounds of the formula (III), but without imposing any limitation: acrylic acid, acrylic acid esters, such as, for example, methyl acrylate and ethyl acrylate, acrylic acid amides, such as, for example, N,N-dimethylacrylamide, acrylonitrile and chloroacrylonitrile, maleic anhydride, maleic acid imides, such as, for example, N-phenylmaleimide, vinyl derivatives, such as, for example, vinylphosphonic acid, dimethyl vinylphosphonate and ω-nitrostyrene.

The compounds of the formula (III) are generally known compounds of organic chemistry.

Formula (IV) provides a general definition of the dienecarboxylic acid derivatives additionally required as starting substances for the preparation of the 2-cyclohexen-1-yl-carboxylic acid derivatives of the formula (II). In this formula (IV), $R^{4'}$, $R^{5'}$ and $R^{6'}$ represent those radicals which have already been mentioned in connection with the description of the compounds of the formula (Ia) according to the invention for these substituents.

The dienecarboxylic acid derivatives of the formula (IV) are known and/or can be prepared in a simple, analogous manner by processes known from the literature (cf. 'Some modern Methods of Organic Synthesis', W Carruthers, Cambridge University Press, 1986, p.125; Acc. Chem. Res., 1979, 146).

Formula (IIb) provides a general definition of the 2-cyclohexene derivatives required as starting substances for carrying out preparation process (B). In this formula (IIb), $R^{1'}$, $R^{2'}$, $R^{3'}$, $R^{4'}$, $R^{5'}$, and $R^{6'}$ and A preferably, or in particular, represent those substituents which have been mentioned above in the description of the new 2-cyclohexen-1-yl-amine derivatives of the formula (Ia) as being preferred, or particularly preferred, for these radicals.

Some of the 2-cyclohexene derivatives of the formula (II) are new and form a part of the present invention.

The compounds which are listed below and which are known, and the enantiomers and isomers thereof, are excepted: methyl 6-formyl-5-{[(phenylmethoxy)-carbonyl]

-amino}-3-cyclohexene-1-carboxylate and methyl 6-(3-oxo-1-propenyl)-5-{[(phenylmethoxy)-carbonyl]-amino}-3-cyclohexene-1-carboxylate (cf. J. Med. Chem., 29, 1–8, 1986; J. Med. Chem., 24, 788–94, 1981), methyl 3-cyclohexene-2-[(trichloroacetyl)-amino]-1-carboxylate, 2,2,2-trichloro-N-(6-formyl-2-cyclohexen-1-yl)-acetamide, ethyl (6-formyl-5-methyl-2-cyclohexen-1-yl)-carbamate, methyl 2-[(ethoxy-carbonyl)-amino]-6-methyl-3-cyclohexene-1-carboxylate, methyl 2-[(ethoxycarbonyl)-amino]-5-methyl-3-cyclohexene-1-carboxylate, methyl 2-[(ethoxycarbonyl)-amino]-3-cyclohexene-1-carboxylate, ethyl 3-{2-[(ethoxycarbonyl)-amino]-6-methyl-3-cyclohexen-1-yl}-2-propenoate, phenyl methyl (6-formyl-5-propyl-2-cyclohexen-1-yl)-carbamate, phenyl methyl (6-formyl-5-methyl-2-cyclohexen-1-yl)-carbamate, methyl 2-[(phenoxycarbonyl)amino]-3-cyclohexene-1-carboxylate and ethyl 3-<6-methyl-2-{[(phenylmethoxy)-carbonyl]-amino}-3-cyclohexen-1-yl>-2-propenoate (cf. J. Am. Chem. Soc., 103, 2816–22, 1981; J. Am. Chem. Soc., 100, 3182–9, 1978; J. Am. Chem. Soc., 100, 5179–85, 1978 and Tetrahedron Lett. 25, 2183–6, 1984), phenyl methyl (6-formyl-5-pentyl-2-cyclohexen-1-yl)-carbamate (cf. J. Org. Chem., 46, 2833–5, 1981) and phenyl methyl {6-formyl-5-[2-(methoxymethoxy)-ethyl]-2-cyclohexen-1-yl}-carbamate (cf. J. Am. Chem. Soc., 105, 5373–9, 1983).

The new 2-cyclohexene derivatives of the formula (IIb) are obtained by (B/a) cyclizing dienophilic compounds of the formula (III)

$$\begin{array}{c} R^{1'} \\ \diagdown \\ \phantom{xx}C=CH-R^{3'} \\ \diagup \\ R^{2'} \end{array} \qquad (III)$$

in which
R$^{1'}$, R$^{2'}$ and R$^{3'}$ have the abovementioned meanings,
with N-acyl-1-amino-1,3-butadiene derivatives of the formula (IVa)

$$A-NH-CH=\underset{\underset{R^{6'}}{|}}{C}-\underset{\underset{R^{5'}}{|}}{C}=CH-R^{4'} \qquad (IVa)$$

in which
R$^{1'}$, R$^{2'}$ and R$^{3'}$ have the abovementioned meanings,
with substituted butadienes of the formula (IVb)

$$R^{15'}-O-CH=\underset{\underset{R^{6'}}{|}}{C}-\underset{\underset{R^{5'}}{|}}{C}=CH-R^{4'} \qquad (IVb)$$

in which
R$^{4'}$, R$^{5'}$ and R$^{6'}$ have the abovementioned meanings and
R$^{15'}$ represents the acetyl radical or the trimethylsilyl radical, initially in a first stage, if appropriate in the presence of a diluent, if appropriate in the presence of a catalyst, if appropriate in the presence of an inert gas and if appropriate under pressure, and reacting the resulting 2-cyclohexene derivatives of the formula (IIc)

(IIc) [cyclohexene ring with substituents R$^{4'}$, R$^{5'}$, R$^{3'}$, R$^{2'}$, R$^{6'}$, R$^{1'}$, and OR$^{15'}$]

in which
R$^{1'}$, R$^{2'}$, R$^{3'}$, R$^{4'}$, R$^{5'}$ and R$^{6'}$ have the abovementioned meanings and
R$^{15'}$ represents the acetyl radical or trimethylsilyl radical, in a second step in a generally customary manner, with 4,4'-dimethoxybenzhydrylamine (DMB) of the formula (V)

$$\left[ H_3CO-\underset{}{\underset{}{\bigcirc}}- \right]_2 CH-NH_2 \qquad (V)$$

(DMB)

if appropriate in the presence of a diluent, such as, for example, tetrahydrofuran, at temperatures from 0° C. to the boiling point of the particular diluent used, and in the presence of a catalyst, such as, for example, tetrakis-(triphenylphosphine)-palladium(O), of the formula (VI), $$[(C_6H_5)_3P]_4Pd \qquad (VI)$$

[cf. J. Org. Chem. 1979, 3451 (1978)], or (B/c) reacting the isocyanates which occur as intermediates in process (A), of the formula (IIa)

(IIa) [cyclohexene ring with substituents R$^{4'}$, R$^{5'}$, R$^{3'}$, R$^{2'}$, R$^{6'}$, R$^{1'}$, and N=C=O]

in which
R$^{1'}$, R$^{2'}$, R$^{3'}$, R$^{4'}$, R$^{5'}$ and R$^{6'}$ have the abovementioned meanings,
with alcohols of the formula (VII)

$$R^{16'}-OH \qquad (VII)$$

in which
R$^{16'}$ represents in each case straight-chain or branched, optionally halogen-substituted alkyl, alkenyl, alkinyl or alkoxyalkyl having 1 to 12 carbon atoms (preferably 1 to 6 carbon atoms) or unsubstituted or substituted phenyl or benzyl, or (B/d) the substituted 2-cyclohexene derivatives of the formula (IIb) are obtained when the 2-cyclohexene derivatives which can be obtained by process (B/a), (B/b) or (B/c), of the formula (IId)

(IId) [cyclohexene ring with substituents R$^{4'}$, R$^{5'}$, R$^{3'}$, CHO, R$^{6'}$, R$^{1'}$, and NH-A]

in which
R$^{1'}$, R$^{3'}$, R$^{4'}$, R$^{5'}$, R$^{6'}$ and A have the abovementioned meanings,
are reduced in a generally customary manner using a complex metal hydride, such as, for example, sodium borohydride, in a suitable solvent, such as, for example, alcohols, such as methanol, ethanol, butanol or isopropanol, and ethers, such as, for example, diethyl ether or tetrahydrofuran, at temperatures from 0° C. to 20° C., and the resulting 2-cyclohexen-1-yl-amine alcohols of the formula (IIe)

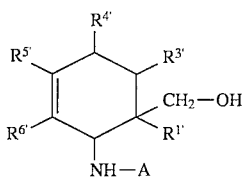

in which

R$^{1'}$, R$^{3'}$, R$^{4'}$, R$^{5'}$, R$^{6'}$ and A have the abovementioned meanings, are converted, for example into esters and ethers, by further reactions on the hydroxyl group. Furthermore, it is possible to obtain acyl derivatives or carbamoyl derivatives of the compounds of the formula (IIb) by reactions with, for example, acyl halides or carbamoyl chlorides, or (B/e) the substituted 2-cyclohexene derivatives of the formula (IIb) are obtained when the 2-cyclohexene derivatives which can be obtained by process (B/a), (B/b) or (B/c), of the formula (IId)

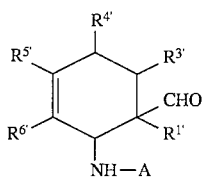

in which

R$^{1'}$, R$^{3'}$, R$^{4'}$, R$^{5'}$, R$^{6'}$ and A have the abovementioned meanings, are reacted with alkanephosphonic acid derivatives of the formula (VIII)

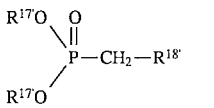

in which

R$^{17'}$ represents methyl or ethyl and

R$^{18'}$ represents the cyano group or represents the alkoxycarbonyl group, if appropriate in the presence of a diluent, if appropriate in the presence of a base and if appropriate in the presence of an inert gas.

Process (B/a) according to the invention for the preparation of the new 2-cyclohexene derivatives of the formula (IIb) is preferably carried out using diluents.

Suitable diluents in this context are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as acetonitrile and propionitrile, amides, such as, for example, dimethylformamide, dimethylacetamide and N-methylpyrrolidone, and dimethyl sulphoxide, tetramethylene sulphone and hexamethylphosphoric triamide.

Suitable inert gases in this context are nitrogen and virtually all noble gases, in particular argon.

When carrying out process (B/a) for the preparation of the 2-cyclohexene derivatives of the formula (IIb), the reaction temperatures can be varied within a relatively wide range. In general, the process is carried out at temperatures between −70° C. and +250° C., preferably between −50° C. and +150° C.

For carrying out process (B/a) for the preparation of the 2-cyclohexene derivatives of the formula (IIb), 1 to 30 moles, preferably 1 to 3 moles, of the dienophilic compound of the formula (III), 0.01 to 20.0 moles, preferably 0.1 to 5.0 moles, of catalyst and if appropriate 0.1 to 5% of a stabilizer which prevents free-radical polymerization, such as, for example, 4-tert-butylcatechol, are generally employed per mole of the N-acyl-1-amino-1,3-butadiene derivatives of the formula (IVa).

The process according to the invention for the preparation of the 2-cyclohexene derivatives of the formula (IIb) is generally carried out under increased pressure. In general, the process is carried out at a pressure of 1 to 200 bar, preferably at 5 to 20 bar.

Suitable catalysts for the preparation of the new 2-cyclohexen-1-yl-carboxylic acid derivatives of the formula (IIb) according to process variant (B/a) are the catalysts which are customary for reactions of this type; Lewis acids, such as, for example, titanium tetrachloride, tin tetrachloride, aluminum trichloride and boron trifluoride etherate, are preferably used.

Under certain circumstances, however, it is also possible to carry out the process for the preparation of the new 2-cyclohexene derivatives of the formula (IIb) without diluents and at a pressure of 1 to 200 bar.

In general, the reactions are carried out in a suitable diluent, and the reaction mixture is stirred for several hours at the specific temperature required. Working up is carried out in each case by customary methods. In general, a procedure is followed in which the reaction mixture is either further concentrated under reduced pressure, or poured into water, and the product is isolated by extraction or filtration and purified by chromatography.

Formula (IVa) provides a general definition of the N-acyl-1-amino-1,3-butadiene derivatives additionally required as starting substances for the preparation of the 2-cyclohexene derivatives of the formula (IIb) according to process variant (B/a). In this formula (IVa), R$^{4'}$, R$^{5'}$, R$^{6'}$ and A represent those radicals which have already been mentioned in connection with the description of the compounds of the formula (Ia) according to the invention for these substituents.

The N-acyl-1-amino-1,3-butadiene derivatives of the formula (IVa) are known and/or can be prepared in a simple, analogous manner by processes known from the literature [cf. J. Org. Chem., 43, 2164 (1978)].

In this process, suitable diluents for carrying out step one of process (B/b) according to the invention are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric triamide.

Suitable inert gases in this process are nitrogen and virtually all noble gases, in particular argon.

When carrying out step one of process (B/b) according to the invention for the preparation of the 2-cyclohexene derivatives of the formula (IIc), the reaction temperatures can be varied within a relatively wide range. In general, the process is carried out at temperatures between −70° C. and +250° C., preferably between −50° C. and +150° C.

For carrying out step one of process (B/b) according to the invention for the preparation of the 2-cyclohexene derivatives of the formula (IIc), 1 to 0.01 mole, preferably 1 to 0.3 mole, of the substituted butadienes of the formula (IVb), 0.01 to 20.0 moles, preferably 0.1 to 5.0 moles, of catalyst and if appropriate 0.1 to 5% of a stabilizer which prevents free-radical polymerization such as, for example, 4-tert-butylcatechol, are generally employed per mole of the dienophilic compounds of the formula (III).

Step one of the process according to the invention for the preparation of the 2-cyclohexene derivatives of the formula (IIc) is generally carried out under increased pressure. In general, the process is carried out at a pressure of 1 to 200 bar, preferably at a pressure of 1 to 20 bar.

Suitable catalysts for step one of process (B/b) according to the invention for the preparation of the new 2-cyclohexene derivatives of the formula (IIc) are the catalysts customary for reactions of this type; Lewis acids, such as, for example, titanium tetrachloride, tin tetrachloride, aluminum trichloride and boron trifluoride etherate, are preferably used.

Under certain conditions, however, it is also possible to carry out step one of process (B/b) according to the invention for the preparation of the new 2-cyclohexene derivatives of the formula (IIc) without diluents and at a pressure of 1 to 200 bar.

In general, the reactions are carried out in a suitable diluent, and the reaction mixture is stirred for several hours at the specific temperature required. Working-up is carried out in each case by customary methods. In general, a procedure is followed in which the reaction mixture is either concentrated under reduced pressure or poured into water, and the product is isolated by extraction or filtration and purified by chromatography.

Formula (IVb) provides a general definition of the butadienes additionally required as starting substances for the preparation of the 2-cyclohexene derivatives of the formula (IIc). In this formula (IVb), $R^{4'}$, $R^{5'}$ and $R^{6'}$ represent those radicals which have already been mentioned in connection with the description of the compounds of the formula (Ia) according to the invention for these substituents.

The substituted butadienes of the formula (IVb) are known and/or can be prepared in a simple, analogous manner by processes known from the literature [cf. J. Org. Chem., 30, 2414 (1965)].

4,4'-Dimethoxybenzhydrylamine (DMB) of the formula (V) and tetrakis(triphenylphosphine)-palladium(O) of the formula (VI), which are additionally required as starting substances for step two of process (B/b) according to the invention, are generally known compounds of organic chemistry [cf. J. Chem. Soc., 7285 (1965)].

Formula (VII) provides a general definition of the alcohols required as starting substances for carrying out process (B/c) according to the invention, and they are generally known compounds of organic chemistry.

Process (B/e) according to the invention for the preparation of the new 2-cyclohexene derivatives of the formula (IIb) is preferably carried out using diluents.

Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as acetonitrile and propionitrile, amides, such as, for example, dimethylformamide, dimethylacetamide and N-methylpyrrolidone, and dimethyl sulphoxide, tetramethylene sulphone and hexamethylphosphoric triamide.

Suitable inert gases in this context are nitrogen and virtually all noble gases, in particular argon.

When carrying out process (B/e) for the preparation of the new 2-cyclohexene derivatives of the formula (IIb), the reaction temperatures can be varied within a relatively wide range. In general, the process is carried out at temperatures between −70° C. and +150° C., preferably between −50° C. and +100° C.

Process (B/e) for the preparation of the new 2-cyclohexene derivatives of the formula (IIb) is generally carried out under atmospheric pressure. Under certain circumstances, however, the process can also be carried out under increased or reduced pressure.

For carrying out process (B/e) for the preparation of the new 2-cyclohexene derivatives of the formula (IIb), in general 1 to 5 moles, preferably 1 to 2 moles, of the alkanephosphonic acid derivatives of the formula (VIII) are generally employed per mole of the 2-cyclohexen-1-yl-amine derivatives of the formula (IId).

Bases which can be employed in process (B/e) according to the invention are all acid-binding agents which can customarily be employed for reactions of this type. Alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate and potassium carbonate, sodium methylate, sodium ethylate, potassium methylate, potassium ethylate, thallium methylate and thallium ethylate, hydrides, such as, for example, sodium hydride, furthermore aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo[5.4.0]-undec-7-ene (DBU) and 1,4-diazabicyclo-[2.2.2-]octane (DABCO), are preferably suitable.

In general, the reactions are carried out in a suitable diluent in the presence of an acid acceptor, and the reaction mixture is stirred for several hours at the specific temperature required. Working up in the process according to the invention is carried out in each case by customary methods.

Formula (VIII) provides a general definition of the alkanephosphonic acid derivatives required as starting substances for carrying out process (B/e) for the preparation of the new 2-cyclohexene derivatives of the formula (IIb), and these alkanephosphonic acid derivatives are known and/or can be prepared in a simple, analogous manner by processes known from the literature.

The compounds of the formula (Ia), (II) and (IIa) to (IIe) can be obtained as mixtures of enantiomers or mixtures of diastereomers.

The invention comprises the pure isomers as well as the mixtures. These mixtures of diastereomers can be resolved by customary methods, for example selective crystallization, from suitable solvents, or chromatography on silica gel or aluminum oxide, to give the components. Racemates can be resolved by customary methods to give the individual enantiomers, for example by salt formation with optically active acids, such as camphorsulphonic acid or dibenzoyltartaric acid, and selective crystallization, or by the formation of derivatives with suitable optically active reagents, separation of the diastereomeric derivatives and renewed splitting or separation on optically active column material.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and, if appropriate, purified by washing with an inert organic solvent.

Suitable salts of metals for the preparation of metal salt complexes of the compounds of the general formula (I) are preferably those which have been described further above.

The metal salt complexes of compounds of the general formula (I) can be obtained in a simple manner by customary processes, for example by dissolving the metal salt in an alcohol, for example ethanol, and adding the solution to compounds of the general formula (I). Metal salt complexes can be isolated in a known manner, for example by filtration, and, if appropriate, they can be purified by recrystallization.

The active compounds according to the invention show a powerful biological action and can be employed in practice for combating undesired pests. For example, the active compounds can be employed for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora*;

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

As plant protection agents, the active compound which can be used according to the invention can be employed with particularly good success protectively for combating Phytophthora species on tomatoes and Venturia species in apples.

In addition, some of the active compounds which can be used according to the invention have a good action against Pythium species, Alternaria species and Cercospora species.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are highly suitable for selectively combating monocotyledon and dicotyledon weeds in monocotyledon crops, in particular using the post-emergence method.

Depending on their particular physical and/or chemical properties, the active compounds which can be used according to the invention can be converted to the customary formulations, such as solutions, emulsions, suspensions, powders, foams, pastes, granules, aerosols, very fine capsules in polymeric substances and in coating compositions for seed, and furthermore ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. Furthermore, 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); N,N-dimethyl-N'-(3-trifluoromethylphenyl)-urea (FLUOMETURON); methyl 2-[4,5-dihydro-4-methyl-4-(1-methylethyl)-5-oxo-1H-imidazol-2-yl]-4(5)-methylbenzoate (IMAZAMETHABENZ); (4-chloro-2-methylphenoxy)-propionic acid (MCPP); N-(1-ethylpropyl)-3,4-dimethyl-2,6-dinitroaniline (PENDIMETHALIN); O-(6-chloro-3-phenyl-pyridazin-4-yl) S-octyl thiocarbonate (PYRIDATE); 4-ethylamino-2-t-butylamino-6-methylthio-s-triazine (TERBUTRYNE) and 3,5,6-trichloro-2-pyridyloxyacetic acid (TRICLOPYR) are also possible.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES:

EXAMPLE 1:

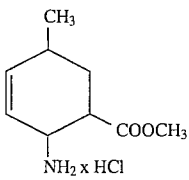 (I-1)

(Process A)

A solution of 5.4 g (0.05 mol) of ethyl chloroformate in 15 ml of acetone is added in the course of 30 minutes at −5° C. to a solution of 10 g (0.05 mol) of methyl 2-carboxy-5-methylcyclohex-3-ene-carboxylate and 8 g (0.062 mol) of N,N-diisopropyl-ethylamine in 30 ml of acetone. After the mixture had remained at 0° C. for a further 30 minutes, an ice-cooled solution of 6.5 g (0.1 mol) of sodium azide in 15 ml of water is added dropwise. The mixture is stirred at 0° C. for 15 minutes and then worked up using water/toluene.

The organic phase, of which a residual volume of about 50 ml is obtained after drying and concentrating, is added dropwise to 50 ml of boiling toluene, and the course of the reaction is monitored by IR spectroscopy. When the transition to the isocyanate is complete, the mixture is evaporated, the residue is taken up in 50 ml of tetrahydrofuran and 50 ml of 1N hydrochloric acid, and the mixture is stirred at 40° C. for 10 hours.

After the mixture has been evaporated completely under reduced pressure, 2.8 g (30% of theory) of 4-methyl-6-carbomethoxy-2-cyclohexen-1-yl-amine hydrochloride are obtained.

$^1$H-NMR data*$^)$ (DMSO, 200 MHz); δ=1.00(3H), 1.50–1.70(1H), 1.85–2.00 and 2.15–2.35(2H), 2.85–3.00(1H), 3.68(3H), 3.80–3.85(2H), 5.70–5.90(2H)

The $^1$H-NMR spectra were recorded in dimethyl sulphoxide (DMSO) with tetramethylsilane (TMS) as the internal standard. The chemical shift is indicated as δ value in ppm.

EXAMPLE 2:

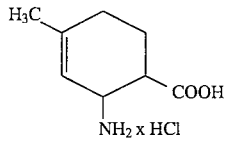 (I-2)

(Process B)

2 g (7.8 mmol) of tert-butyl (3-methyl-6-carboxy-2-cyclohexen-1-yl)-carbamate are introduced in 5 ml of 1N hydrochloric acid. After the mixture has been kept at 50° C. for 4 hours it is evaporated to dryness, and 1.3 g (87% of theory) of 3-methyl-6-carboxy-2-cyclohexen-1-yl-amine hydrochloride are obtained as a white solid of melting point 156°–163° C.

The end products of the formula (I)

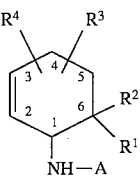 (I)

which are listed in Table 1 below are obtained analogously to the methods described in Examples 1 and 2 and following the instructions in the descriptions of the processes according to the invention:

TABLE 1

| Ex. No. | $R^1$ | $R^2$ | $R^3$ | $R^4$ | A | Physical constants |
|---|---|---|---|---|---|---|
| I-3 | H | COOH | H | 4-CH$_3$ | H | m.p.: 190–193° C. × HCl/uniform cis diastereomer |
| I-4 | H | COOH | H | H | H | m.p.: 169–172° C. × HCl/uniform cis diastereomer |
| I-5 | H | COOCH$_3$ | H | H | H | $^1$H-NMR*$^)$(CDCl$_3$, 200 MHz): δ = 1.65–2.20(6H), 2.57–2.68(1H), 3.60–3.70(2H), 3.71 (3H), 5.78(2H) |
| I-6 | H | COOH | 3,4-(CH$_2$—CH$_2$—CH$_2$—CH$_2$)— | | H | m.p.: 185–205° C. × HCl |
| I-7 | H | COOCH$_3$ | H | H | H | $^1$H-NMR*$^)$; (CDCl$_3$, 200 MHz): δ = 1.90–2.4(4H), 3.03–3.17 (1H), 3.78(3H), 4.20(1H), 6.00(2H), 8.25–9.65(3H) × HCl |
| I-8 | H | COOH | H | 4-C$_6$H$_5$ | H | m.p.: 175–190° C. ×HCl |
| I-9 | H | COOCH$_3$ | H | 4-C$_6$H$_5$ | H | $^1$H-NMR*$^)$(DMSO, 200 MHz): δ = 2.75–2.85(1H), 3.30–3.43 (1H), 3.65 and 3.68(3H), 5.75–6.00(2H), 7.10–7.40(5H) |
| I-10 | H | COOCH$_2$CH$_2$OCH$_3$ | H | 4-CH$_3$ | H | $^1$H-NMR*$^)$(DMSO, 200 MHz): δ = 1.05(3H), 3.30(3H), 5.75–5.95(2H), 8.10–8.50(3H) |

TABLE 1-continued

| Ex. No. | R¹ | R² | R³ | R⁴ | A | Physical constants |
|---|---|---|---|---|---|---|
| I-11 | H | COOH | H | 4-C₃H₇ | H | m.p.: 180–185° C. × HCl |
| I-12 | Cl | COOH | H | 4-CH₃ | H | m.p.: 208–214° C. × HCl |
| I-13 | H | COOH | H | 4-C₂H₅ | H | m.p.: 168–178° C. × HCl |
| I-14 | H | COOH | H | 3-C₂H₅ | H | m.p. 140–150° C. × HCl |
| I-15 | CH₃ | COOCH₃ | H | H | H | ¹H-NMR*⁾ (DMSO, 200 MHz): δ = 1.16 and 1.29 (isomer, 3H), 3.65(3H), 5.60–5.70 and 5.85–6.00(2H), 8.20–8.50 (3H)/× HCl |
| I-16 | H | COOH | H | 3-C₄H₉ | H | m.p.: 180–188° C. × HCl |
| I-17 | H | CN | H | 4-CH₃ | H | |
| I-18 | H | CN | H | 4-C₂H₅ | H | ¹H-NMR (DMSO, 200 mHz): δ = 1.05(3H), 1.80–2.10 and 2.20–2.40(3H), 3.48(1H), 3.95 (1H), 5.65–5.95(2H), 8.60–9.00(3H)/ × HCl |
| I-19 | Cl | CN | H | 4-CH₃ | H | m.p.: 130–135° C. × HCl |
| I-20 | H | NO₂ | 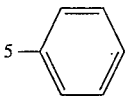 5- | 4-CH₃ | H | ¹H-NMR (CDCl₃, 200 MHz): δ = 1.15(3H), 1.20–1.40 and 1.85–2.55(5H), 3.60(1H), 5.60–5.85(2H) |
| I-21 | H | —CH=CH—C(=O)—OC₂H₅ | H | 4-CH₃ | H | m.p.: 215–221° C. × HCl |
| I-22 | H | —CH=CH—COOH | H | H | H | ¹H-NMR*⁾ (CDCl₃, 200 MHz): δ = 1.02(3H), 1.29(3H), 4.18(2H), 5.55–6.00(3H), 6.83–7.10(1H) |
| I-23 | H | —CH=CH—C(=O)—OC₂H₅ | H | 4-CH₃ | H | m.p.: 186–218° C. × HCl |
| I-24 | H | —CH₂—OH | H | 4-CH₃ | H | m.p.: 191–214° C. × HCl |
| I-25 | H | 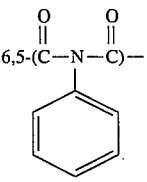 6,5-(C(=O)—N—C(=O))— | | 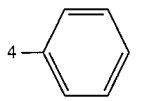 4- | H | m.p.: 71–83° C. × HCl |
| I-26 | H | 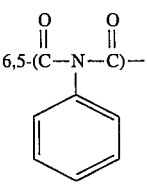 6,5-(C(=O)—N—C(=O))— | 4-CH₃ | | H | m.p.: 51–53° C. × CF₃COOH |
| I-27 | H | 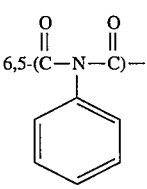 6,5-(C(=O)—N—C(=O))— | H | H | H | m.p.: 80–83° C. × CF₃COOH |
| I-28 | H | —CH₂O—COCH₃ | H | 4-CH₃ | H | m.p.: 75–81° C. × CF₃COOH |
| I-29 | H | —CO—N(CH₃)₂ | H | H | H | ¹H-NMR*⁾ (CDCl₃, 200 MHz): |

TABLE 1-continued

| Ex. No. | R¹ | R² | R³ | R⁴ | A | Physical constants |
|---|---|---|---|---|---|---|
| | | | | | | δ = 1.08(3H), 2.10(3H), 4.02–4.28(2H), 5.76–6.00 (2H), 8.10–8.55(3H) × HCl |
| I-30 | H | —CO—N(CH₃)₂ | H | H | H | IR: 3500–3350, 1655 cm⁻¹ |
| I-31 | H | —CO—N(CH₃)₂ | H | 4-CH₃ | H | IR: 1670 cm⁻¹ × CF₃COOH |
| | | | | | | IR: 1670 cm⁻¹ × CF₃COOH |
| I-32 | H | —CO—NH—C₆H₅ | H | 4-CH₃ | H | m.p.: 111–127° C. |
| I-33 | H | —CO—OCH(CH₃)₂ | H | 4-CH₃ | H | ¹H-NMR*⁾ (CDCl₃, 200 mHz): δ = 1.05(3H), 1.26(6H), 5.08(1H), 5.53–5.80(2H) |
| I-34 | H | —CO—CH₂—C₆H₅ | H | 4-CH₃ | H | ¹H-NMR*⁾ (CDCl₃, 200 MHz): δ = 1,05(3H), 5.18(2H), 5.60–5.85(2H), 7.25–7.40(5H) |
| I-35 | F | COOH | H | 4-CH₃ | H | ¹H-NMR*⁾ (CDCl₃, 200 MHz): δ = 1.16(3H), 1.80–2.60(3H), 3.83–4.00(1H), 5.65–5.78 and 6.00–6.13 (2H) |
| I-36 | H | —COO—C₄H₉-n | H | 4-CH₃ | H | ¹H-NMR*⁾ (DMSO, 200 MHz): δ = 0.89(3H), 1.03(3H), 2.84–2.98(1H), 4.00–4.20(2H), 5.70–5.90(2H), 8.10–8.40(3H) |
| I-37 | H | —COOC₄H₉-n | H | 4-CH₃ | H | IR: 3500–3410, 1735 cm⁻¹ |
| I-38 | H | —COOC₂H₅ | H | 4-CH₃ | H | IR: 3500–3400, 1735 cm⁻¹ |
| I-39 | H | CN | H | 4-C₂H₅ | H | ¹H-NMR*⁾ (CDCl₃, 200 MHz): δ = 0.92(3H), 1.27–1.70(5H), 1.90–2.10(2H), 2.78–2.88 (1H), 3.53–3.60(1H), 5.65–5.80(2H) |
| I-40 | H | —CH₂OH | H | 4-CH₃ | H | MS: m/z (rel. int.): 141 (7), 99 (32), 83 (100) |
| I-41 | H | —CH₂OH | H | H | H | ¹H-NMR*⁾ (DMSO, 200 MHz): δ = 1.30–2.10(5H), 5.63–5.82 and 5.90–6.08(2H), 8.00–8.40 (3H) |
| I-42 | H | —COOH | H | 5-CH(CH₃)₂ | H | m.p.: 189–205° C./× HCl |
| I-43 | H | —COOH | H | 4-CH₃ | H | m.p.: 130–138° C. diastereomer ratio 70:30/× HCl |
| I-44 | H | 6,5-(C(=O)—O—CH₂—CH₂)— | | 4-CH₃ | H | ¹H-NMR*⁾ (CDCl₃, 200 MHz): δ = 0.80(3H), 1.80–2.20 and 2.30–2.50 (4H), 2.90–3.05 (1H), 4.20–4.60(2H), 6.05–6.20 and 6.30–6.40(2H), 7.30 (1H)/× HCl |
| I-45 | H | —COOC₂H₅ | 5-CH₃ | H | H | |
| I-46 | H | —COOH | H | 4-CH₃ | H | ¹H-NMR*⁾ (DMSO, 200 MHz): δ = 0.93(3H), 1.21(3H), 2.55–2.65(1H), 4.10–4.25(2H), 5.70–6.63(2H), 8.10–8.30 (3H)/× HCl |
| I-47 | H | —COOH | H | 4-CH₃ | H | Optical rotation: [α]$_D^{20}$ = +76.6 (C = 0.3, H₂O) × HCl enantiomer of I-3 |
| I-48 | H | —CONH—C₆H₅ | H | 4-CH₃ | H | Optical rotation: [α]$_D^{20}$ = −84.1 (C = 0.3, H₂O) × HCl enantiomer of I-3 |
| I-49 | H | —COOCH(CH₃)₂ | H | 4-CH₃ | H | m.p.: 128–133° C. × HCl |
| I-50 | H | —P(=O)(OH)(OCH₃) | H | 4-CH₃ | H | ¹H-NMR*⁾ (CDCl₃, 200 MHz): δ = 1.15(3H), 1.25(6H), 2.71–2.85(1H), 5.00–5.18(1H), 5.87–6.08(2H), 8.30–8.70 (3H)/× HCl |

TABLE 1-continued

| Ex. No. | R¹ | R² | R³ | R⁴ | A | Physical constants |
|---|---|---|---|---|---|---|
| | | | | | | MS (FAB): 205 [M⁺] × HCl |
| I-51 | H | —COOH | H | 4-CH₃ | H × | HO₂C—CH₂—CH(OH)—CO₂H <br> ¹H-NMR (DMSO): δ = 1.00 (3H), 1.40 (m, 1H); 2.20–2.60 (6H); 3.75 (1H); 4.05 (1H); 5.60–5.90 (2H). |
| I-52 | H | —COOH | H | 4-CH₃ | H × | 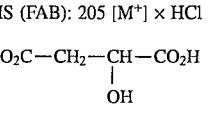 CH₃—C₆H₄—SO₃H <br> ¹H-NMR (DMSO): δ 1.00 (3H); 1.50 (m, 1H); 2.25 (3H); 2.80 (1H); 5.60–5.90 (2H); 7.10 (2H); 7.50 (2H). |
| I-53 | H | —COOH | H | 4-CH₃ | H × | CuSO₄ m.p.: 210–219° C. (decomp.) |
| I-54 | H | —COOH | H | 4-CH₃ | H × | HBr ¹H-NMR (DMSO): δ = 1.00 (3H), 1.50 (1H); 2.80 (1H); 5.60–5.90 (2H); 7.90 (br, 3H). |
| I-55 | H | —COOH | H | 4-CH₃ | H × | CH₃CO₂H ¹H-NMR (DMSO): δ = 0.95 (3H); 1.85 (3H); 5.60–5.80 (2H). |
| I-56 | H | —COOH | H | 4-CH₃ | H × | HCl Isomer zu I-3 <br> ¹H-NMR (CD₃OD): δ = 1.06 (3H); 1.83 (1H); 2.00 (1H); 2.38 (1H); 2.81 (1H); 4.08 (1H); 5.60 (1H); 6.00 (1H). |
| I-57 | H | —CH₂—OH | H | 4-CH₃ | H × | HCl ¹H-NMR (DMSO): δ = 1.00 (3H); 3.45 (2H); 5.70–5.90 (2H); 8.06 (3H). |
| I-58 | H | —COOH | H | 4-CH₃ | H | (zwitterion) m.p.: 208–211° C. |
| I-59 | H | —CO₂CH₃ | H | 4-CH₃ | H × | 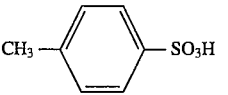 Strongly hygroscopic |
| I-60 | H | —CO₂CH₃ | H | 4-CH₃ | H × | HO₂CCH₂C(OH)—(CO₂H)CH₂CO₂H hygroscopic |
| I-61 | H | —CO₂CH₃ | H | 4-CH₃ | H × | HO₂CCO₂H m.p.: 152–158° C. |
| I-62 | H | —CO₂CH₃ | H | 4-CH₃ | H × | 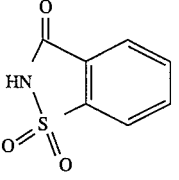 HO₃S—C₆H₄—CH₃ m.p.: 125–128° C. |
| I-63 | H | —CO₂CH₃ | H | 4-CH₃ | H × | CH₃CO₂H m.p.: 89,5–90° C. |
| I-64 | H | —CO₂(CH₂)₂OCH₃ | H | 4-CH₃ | H | $n_D^{20}$ 1.4763 |
| I-65 | H | —CO₂CH₃ | H | 4-CH₃ | H | $n_D^{20}$ 1.4791 |
| I-66 | H | —CO₂H | H | 4-CH₃ | H × | 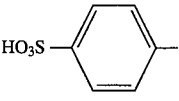 <br> ¹H-NMR (DMSO): δ 1.00 (3H); 1.50 (1H); 2.00 (1H); 2.30 (1H); 2.85 (1H); 3.90 (1H); 5.60–5.95 (2H); 7.61 (5H). |
| I-67 | H | —CO₂H | H | 4-CH₃ | H × | HO₂CCO₂H ¹H-NMR (DMSO): δ = 1.05 (3H), 1.45 (1H); 2.05 |

TABLE 1-continued

| Ex. No. | R¹ | R² | R³ | R⁴ | A | Physical constants |
|---|---|---|---|---|---|---|
| | | | | | | (1H), 2.31 (1H); 2.85 (1H); 3.80 (1H); 5.60–5.80 (2H). |
| I-68 | H | —CO$_2$(CH$_2$)$_3$CH$_3$ | H | 4-CH$_3$ | H × 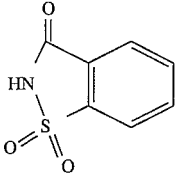 | wax-like solid |
| I-69 | H | —CO$_2$CH$_2$CH(CH$_3$)$_2$ | H | 4-CH$_3$ | H | $^1$H-NMR (CDCl$_3$): δ = 0.90– 1.08 (9H); 2.60–2.73 (1H); 3.90 (2H); 5.60–5.80 (2H). |
| I-70 | H | —CO$_2$CH$_2$CH(CH$_3$)$_2$ | H | 4-CH$_3$ | H × | HCl $^1$H-NMR (DMSO): δ = 0.85– 1.05 (9H); 2.90–3.00 (1H); 3.90 (2H); 5.70–5.90 (2H); 5.20 (3H). |
| I-71 | H | —CO$_2$H | H | 4-CH$_3$ | H × | Cu(OAc)$_2$ MS (FAB): 155 [M$^+$ — Cu(Ac)$_2$] |
| I-72 | H | —CO$_2$H | H | 4-CH$_3$ | H × | HO$_2$CCH$_2$CO$_2$H MS (FAB): 259 [M$^+$] |
| I-73 | H | —CO$_2$H | H | 4-CH$_3$ | H × | HO$_2$C—CH=CH—CH=CH—CH$_3$ MS (FAB): 267 [M$^+$] |
| I-74 | H | —CO$_2$H | H | CH(CH$_3$)$_2$ | H × | HCl m.p.: 203–206° C. (decomp.) |
| I-75 | H | —CO$_2$H | H | H | zwitterion | m.p.: 98° C. |
| I-76 | H | —CO$_2$H | 3-CH$_3$ | 4-CH$_3$ | H × | HCl m.p.: 133–135° C. |
| I-77 | H | —CO$_2$H | 3-C$_6$H$_5$ | 4-CH$_2$CH(CH$_3$)$_2$ | H × | HCl m.p.: 140–145° C. |
| I-78 | H | —CO$_2^-$Na$^+$ | H | 4-CH$_3$ | H | m.p.: >250° C. (decomp.) |
| I-79 | H | —CO$_2^-$NH$_4^+$ | H | 4-CH$_3$ | H | m.p.: >250° C. (decomp.) |
| I-80 | | —CO$_2$CH$_3$ | 3-C$_6$H$_5$ | 4-CH$_2$CH(CH$_3$)$_2$ | H | $^1$H-NMR (CDCl$_3$): δ = 0.75– 0.95 (9H); 2.65–2.85 (1H); 3.75 (3H), 5.90 (1H); 7.15– 7.40 (5H). |
| I-81 | H | —CO$_2$H | H | H | H × | HO$_2$CCO$_2$H m.p. 147–150° C. (decomp.) |
| I-82 | H | —CO$_2$H | H | H | H × 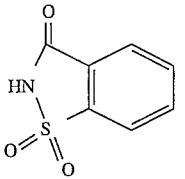 | m.p.: 106–112° C. (decomp.) |
| I-83 | H | —CO$_2$H | 3-C$_6$H$_5$ | 4-CH(CH$_3$)$_2$ | H × | HCl m.p.: 245–248° C. |
| I-84 | H | —CO$_2$H | 3-CH(CH$_3$)$_2$ | 4-CH$_2$CH(CH$_3$)$_2$ | H × | HCl m.p.: 210–218° C. |
| I-85 | H | —CN | 3-CH(CH$_3$)$_2$ | 4-CH$_2$CH(CH$_3$)$_2$ | H × | HCl m.p.: 164° C. |
| I-86 | H | —CN | 3-C$_6$H$_5$ | 4-CH(CH$_3$)$_2$ | H × | HCl m.p.: 233–261° C. |
| I-87 | H | —CO$_2$C$_2$H$_5$ | H | H | H × | HCl m.p.: 139–148° C. |
| I-88 | H | —CO$_2$CH(CH$_3$)$_2$ | H | H | H × | HCl m.p.: 188–188.5° C. |
| I-89 | H | —CO$_2$C$_6$H$_5$ | H | 4-CH$_3$ | H | m.p.: 117° C. |
| I-90 | H | —CO$_2$C$_6$H$_5$ | H | 4-CH$_3$ | H × | HCl $^1$H-NMR (DMSO) δ = 1.00 (3H); 1.40 (1H); 2.80 (1H); 5.65–5.95 (2H); 7.20 (5H). |
| I-91 | H | —CO$_2$CH$_3$ | H | 4-CH(CH$_3$)$_2$ | H × | HCl MS: 197 [M$^+$ - HCl] |
| I-92 | H | 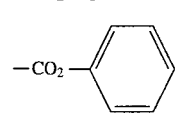 | H | 4-CH$_3$ | H × 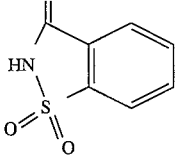 | MS: 231 [M$^+$-183] |
| I-93 | H | —CO$_2$H | H | H | H × | HCl (Enantiomer) m.p.: 210–213.5° C. |
| I-94 | H | —CO$_2$H | H | H | H × | HCl (Enantiomer) m.p.: 208–210° C. |

TABLE 1-continued

| Ex. No. | $R^1$ | $R^2$ | $R^3$ | $R^4$ | A | Physical constants |
|---|---|---|---|---|---|---|
| I-95 | H | $-CO_2H$ | H | 4—⟨O⟩ (cyclic ether) | H × | HCl MS: $M^+$ 207<br>FAB-spectroscopy |
| I-96 | H | $-CO_2CH_3$ | H | H | H × | HCl (Enantiomer)<br>MS (FAB): 191 $[M^+]$ |
| I-97 | H | $-CO_2CH_3$ | H | H | H × | HCl (Enantiomer)<br>MS (FAB): 191 $[M^+]$ |
| I-98 | H | $CO_2CH_2-C_6H_5$ | H | H | H | $^1$H-NMR (CDCl$_3$): δ = 1.50 (2H); 2.60–2.70 (1H); 3.67 (1H); 5.15 (2H); 5.75 (2H); 7.32 (5H). |
| I-99 | H | $CO_2CH_2$-2,4-$Cl_2C_6H_3$ | H | 4-$CH_3$ | H | $^1$H-NMR (CDCl$_3$): δ = 1.05 (d, 3H); 2.73–2.85 (1H); 5.22 (2H); 5.78 (2H); 7.22–7.40 (3H). |
| I-100 | H | $CO_2CH_2-C_6H_5$ | H | H | H × | HCl MS: 231 $[M^+ - 36]$ |
| I-101 | H | $CO_2CH_2$-2,4-$Cl_2C_6H_3$ | H | 4-$CH_3$ | H × | HCl MS: 313 $[M^+ - 36]$ |
| I-102 | H | $CO_2CH_2$-2-$ClC_6H_4$ | H | 4-$CH_3$ | H | $^1$H-NMR (CDCl$_3$): δ = 1.05 (3H); 2.60 (2H); 2.65–2.77 (1H); 5.26 (2H); 5.56–5.80 (2H); 7.20–7.50 (4H). |
| I-103 | H | $CO_2CH_2$-3-$ClC_6H_4$ | H | 4-$CH_3$ | H | $^1$H-NMR (CDCl$_3$): δ = 1.06 (3H); 2.68–2.80 (1H); 3.77 (1H); 5.15 (2H); 5.60–5.80 (2H); 7.3 (4H). |
| I-104 | H | $CO_2CH_2$-4-$ClC_6H_4$ | H | 4-$CH_3$ | H | $^1$H-NMR (CDCl$_3$): δ = 1.05 (3H); 2.65–2.78 (1H); 5.15 (2H); 5.60–5.80 (2H); 7.32 (4H). |
| I-105 | H | $CO_2CH_2$-4-$NO_2C_6H_4$ | H | 4-$CH_3$ | H | m.p.: 118–124° C. |
| I-106 | H | $CO_2CH_2$-2-$ClC_6H_4$ | H | 4-$CH_3$ | H × | HCl MS: 279 $[M^+ - 36]$ |
| I-107 | H | $CO_2CH_2$-3-$ClC_6H_4$ | H | 4-$CH_3$ | H × | HCl MS: 279 $[M^+ - 36]$ |
| I-108 | H | $CO_2CH_2$-4-$ClC_6H_4$ | H | 4-$CH_3$ | H × | HCl m.p.: 167° C. |
| I-109 | H | $CO_2CH_2$-4-$NO_2C_6H_4$ | H | 4-$CH_3$ | H × | HCl m.p.: 196–202° C. |
| I-110 | H | $CO_2CH_2$-2-$ClC_6H_4$ | H | H | H | $^1$H-NMR (CDCl$_3$): δ = 1.80–2.15 (4H); 2.65–2.85 (3H); 5.29 (2H); 5.78 (2H); 7.20–7.50 (4H). |
| I-111 | H | $CO_2CH_2$-3-$ClC_6H_4$ | H | H | H | $^1$H-NMR (CDCl$_3$): δ = 1.75–2.15 (4H), 2.56 (2H), 2.65–2.75 (1H); 5.15(2H); 5.79 (2H); 7.20–7.40 (4H). |
| I-112 | H | $CO_2CH_2$-4-$ClC_6H_4$ | H | H | H | m.p.: 142° C. |
| I-113 | H | $CO_2CH_2$-4-$NO_2C_6H_4$ | H | H | H | $^1$H-NMR (CDCl$_3$): δ = 1.75–2.15 (6H); 5.28 (2H); 5.78 (2H); 7.55 (2H); 8.20 (2H). |
| I-114 | H | $CO_2CH_2$-2-$ClC_6H_4$ | H | H | H × | HCl $^1$H-NMR (DMSO): δ = 1.95–2.12 (4H); 5.15–5.35 (2H); 5.65–6.05 (2H); 7.30–7.60 (4H); 8.25 (3H). |
| I-115 | H | $CO_2CH_2$-3-$ClC_6H_4$ | H | H | H × | HCl $^1$H-NMR (DMSO): δ = 1.95–2.12 (4H); 3.10 (1H); 5.19 (2H); 7.39 (4H); 8.25 (3H). |
| I-116 | H | $CO_2CH_2$-4-$ClC_6H_4$ | H | H | H × | HCl MS: 265 $[M^+ - 36]$ |
| I-117 | H | $CO_2CH_2$-4-$NO_2C_6H_4$ | H | H | H | $^1$H-NMR (DMSO); δ = 1.90–2.15 (4H); 5.33 (2H); 5.70–6.05 (2H); 7.70 (2H); 8.20 (2H); 8.45 (3H). |
| I-118 | H | $CO_2CH_2$-3,5-$(OCH_3)_2C_6H_3$ | H | 4-$CH_3$ | H | $^1$H-NMR (CDCl$_3$): δ = 1.03 (3H); 3.79 (6H); 5.10 (2H); 5.58–5.80 (2H); 6.40–6.55 (3H). |
| I-119 | H | $CO_2CH_2$-2-$NO_2C_6H_4$ | H | 4-$CH_3$ | H | $^1$H-NMR (CDCl$_3$): δ = 1.05 (3H); 5.56 (2H); 5.60–5.85 (2H); 7.45–7.70 (3H); 8.10 (1H). |
| I-120 | H | $CO_2CH_2$-2,4-$Cl_2C_6H_3$ | H | H | H | $^1$H-NMR (CDCl$_3$): δ = 2.65–2.78 (1H); 2.70 (1H); 5.21 (2H); 5.78 (2H); 7.20–7.35 (3H). |
| I-121 | H | $CO_2CH_2$-3-$NO_2C_6H_4$ | H | H | H | MS: 276 $[M^+]$ |
| I-122 | H | $CO_2CH_2$-3,5-$(OCH_3)_2C_6H_3$ | H | H | H | $^1$H-NMR (CDCl$_3$): δ = 3.79 (6H); 5.10 (2H); 5.80 (2H); |

TABLE 1-continued

| Ex. No. | R¹ | R² | R³ | R⁴ | A | Physical constants |
|---|---|---|---|---|---|---|
| I-123 | H | $CO_2CH_2$-3-$NO_2C_6H_4$ | H | 4-$CH_3$ | H | 6.40–6.60 (3H). $^1$H-NMR (CDCl$_3$): δ = 1.05 (3H); 2.68–2.80 (1H); 5.28 (2H); 5.55–5.80 (2H); 7.50–7.75 (2H); 8.15–8.30 (2H). |
| I-124 | H | $CO_2CH_2$—$C_6H_5$ | H | 4-CH(CH$_3$)$_2$ | H | $^1$H-NMR (CDCl$_3$): δ = 0.90 (6H); 2.60–2.70 (1H); 5.17 (2H); 5.60–5.85 (2H); 7.35 (5H). |
| I-125 | H | $CO_2CH_2$-3,5-(OCH$_3$)$_2$C$_6$H$_3$ | H | 4-CH$_3$ | H × | HCl $^1$H-NMR (DMSO): δ = 8.29 (—NH$_3^\oplus$, 3H). |
| I-126 | H | $CO_2CH_2$-2-NO$_2$C$_6$H$_4$ | H | 4-CH$_3$ | H × | HCl $^1$H-NMR (DMSO): δ = 8.35 (—NH$_3^\oplus$, 3H). |
| I-127 | H | $CO_2CH_2$-2,4-Cl$_2$C$_6$H$_3$ | H | H | H × | HCl $^1$H-NMR (DMSO): δ = 8.25 (—NH$_3^\oplus$, 3H). |
| I-128 | H | $CO_2CH_2$-3-NO$_2$C$_6$H$_4$ | H | H | H × | HCl $^1$H-NMR (DMSO): δ = 8.40 (—NH$_3^\oplus$, 3H). |
| I-129 | H | $CO_2CH_2$-3,5-(OCH$_3$)$_2$C$_6$H$_3$ | H | H | H × | HCl MS: 291 [M$^+$ - 36] |
| I-131 | H | $CO_2CH_2C_6H_5$ | H | 4-CH(CH$_3$)$_2$ | H × | HCl $^1$H-NMR (DMSO): δ = 0.85 (6H); 1.55–2.10 (4H); 5.20 (2H); 5.80–6.00 (2H); 7.38 (5H); 8.35 (3H). |
| I-132 | H | $CO_2CH_2$-3,5-Cl$_2$C$_6$H$_3$ | H | H | H | $^1$H-NMR (CDCl$_3$): δ = 1.75–2.15 (6H); 2.65–2.80 (1H); 5.22 (2H); 5.78 (2H); 7.20–7.50 (3H). |
| I-133 | H | $CO_2CH_2$-2,6-Cl$_2$C$_6$H$_3$ | H | H | H | $^1$H-NMR (CDCl$_3$): δ = 1.75–2.15 (6H); 5.40 (2H); 5.75 (2H); 7.20–7.40 (3H). |
| I-134 | H | $CO_2CH_2$-3,5-Cl$_2$C$_6$H$_3$ | H | H | H × | HCl $^1$H-NMR (DMSD): δ = 8.43 (—NH$_3^\oplus$, 3H). |
| I-135 | H | $CO_2CH_2$-2,6-Cl$_2$C$_6$H$_3$ | H | H | H × | HCl $^1$H-NMR (DMSO): δ = 8.25 (—NH$_3^\oplus$, 3H). |

*⁾The $^1$H-NMR spectra were recorded in deuterochloroform (CDCl$_3$) or dimethyl sulphoxide (DMSO) with tetramethylsilane (TMS) as the internal standard. The chemical shift is indicated as δ value in ppm.

PREPARATION OF THE STARTING SUBSTANCES:

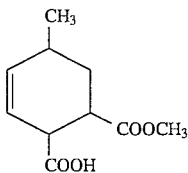
(II)

A solution of 10 g (0.089 mol) of sorbic acid, 24.1 ml (0.27 mol) of methyl acrylate, 0.1 g (0.6 mmol) of 4-tert butylcatechol and 100 ml of dioxane is reacted for 30 hours at a temperature of 110° C. at 5 bar. The dioxane is distilled off, and the polar by-products are separated off using the eluent mixture petroleum ether/ethyl acetate (2: 1). 13.2 g (75% of theory) of methyl 2-carboxy-5-methylcyclohex-3-ene-carboxylate are obtained as a mixture of isomers.

$^1$H-NMR*⁾ (CDCl$_3$, 200 MHz): δ=1.05 (d, 3H); 3.65 (s, 3H), 5.40–5.90 (m, 2H).

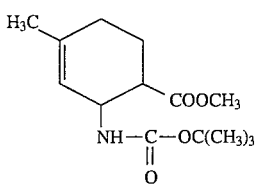
(IIb-1)

(Process B/a)

A solution of 20.5 g (0.11 mol) of tert-butyl (trans-3-methyl-1,3-butadiene-1)-carbamate, 34 g (0.39 mol) of methyl acrylate, 1 g (6 mmol) of 4-tert-butylcatechol and 90 ml of dioxane is reacted for 20 hours at 110° C. and 6 bar. After the excess methyl acrylate has been distilled off, the mixture is separated on silica gel using the eluent mixture petroleum ether/ethyl acetate (5:1).

24 g (80% of theory) of tert-butyl (3-methyl-6-carbomethoxy-2-cyclohexen-1-yl)-carbamate are obtained as a waxy solid.

$^1$H-NMR*⁾ (CDCl$_3$, 200 MHz): δ=1.42(9H), 1.68 (3H), 1.70–2.00(4H), 2.70(1H), 3.68(3H), 4.50(1H), 4.80 (1H), 5.30–5.45(1H)

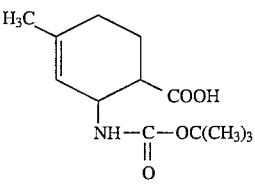
(IIb-2)

5 g (18.6 mmol) of tert-butyl (3-methyl-6-carbomethoxy-2-cyclohexen-1-yl)-carbamate are introduced into 40 ml of 1N sodium hydroxide solution, and the mixture is stirred at 50° C. until a clear solution has formed. The solution is extracted once using diethyl ether, and a pH of 1 is then established at 0° C. using concentrated hydrochloric acid. After the mixture has been extracted using diethyl ether and evaporated, 3.5 g (74% of theory) of tert-butyl 3-methyl-6-carboxy -2-cyclohexen-1-yl-carbamate of melting point 132°–136° C. are obtained.

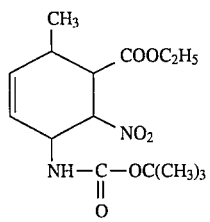
(IIb-3)

(Process B/a)

A solution of 18.8 g (0.13 mol) of ethyl trans -3-nitroacrylate in 100 ml of benzene is added dropwise at room temperature to a solution of 20.1 g (0.11 mol) of tert-butyl trans-1,3-pentadiene-1-carbamate and 0.25 g (1.5 mmol) of 4-tert butylcatechol in 50 ml of benzene, and the solution is stirred for 20 hours at room temperature. The solution is concentrated to half the volume, and crystals are allowed to form at +4° C. 18.3 g (53% of theory) of ethyl 3-(N-tert-butyloxy-carbonylamino) -2-nitro-6-methyl-4-cyclohexene-carboxylate of melting point 139°–45° C. are obtained.

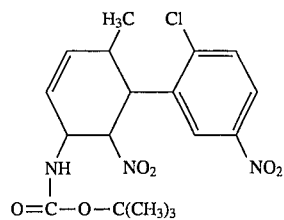
(IIb-4)

(Process B/a)

10 g (55 mmol) of tert-butyl (trans-1,3-pentadiene-1)-carbamate, 12.4 g (55 mmol) of trans-2-(2-chloro-5-nitrophenyl)-nitroethene and 0.6 g (3.6 mmol) of 4-tert-butylcatechol in 100 ml of dioxane are reacted for 30 hours at 110° C. and 4 bar. The reaction mixture is evaporated and recrystallized twice from ethanol.

7 g (31% of theory) of tert-butyl 4-methyl-5-(2-chloro-5-nitro-phenyl)-6-nitro-2-cyclohexen-1-yl-carbamate of melting point 195°–203° C. are obtained.

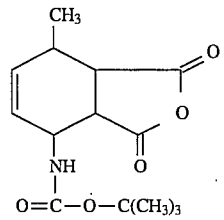
(IIb-5)

(Process B/a)

A solution of 1 g (5.5 mmol) of tert-butyl trans-1,3-pentadiene-1-carbamate, 1.1 g (11 mmol) of maleic anhydride, 40 mg (0.2 mmol) of 4-tert-butylcatechol and 3 ml of dioxane is heated at 100° C. for 2 hours. The mixture is evaporated to dryness, and 0.8 g (52% of theory) of tert-butyl (4-methyl-cyclohex-2-ene -5,6-dicarboxylic anhydride-1-yl)-carbamate of a melting point of 180°–182° C. is obtained after recrystallization from benzene.

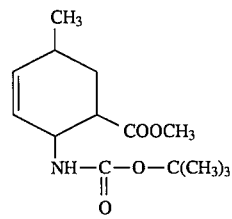
(IIb-6)

(Process B/c)

A solution of 5.4 g (0.05 mol) of ethyl chloroformate in 15 ml of acetone is added to a solution of 10 g (0.05 mol) of methyl 2-carboxy-5-methylcyclohex-3-ene-carboxylate and 8 g (0.062 mol) of N,N-diisopropylethylamine in 30 ml of acetone at −5° C. in the course of 30 minutes. After the mixture has remained at 0° C. for 30 more minutes, an ice-cooled solution of 6.5 g (0.1 mol) of sodium azide in 15 ml of water is added dropwise. The mixture is stirred for 15 minutes at 0° C. and then worked up using water/toluene.

The toluene phase, which is concentrated to approximately 50 ml, is then added dropwise to a solution, boiling under reflux, of 3 g (0.04 mol) of tertbutanol and 25 mg (0.15 mmol) of tert-butylcatechol in 20 ml of toluene. The course of the reaction is monitored by IR spectroscopy.

The mixture is allowed to cool to room temperature and concentrated. After separation by column chromatography on silica gel using the eluent petroleum ether/ethyl acetate (6:1), 4 g (30% of theory) of tert-butyl (4-methyl-6-carbomethoxy-2-cyclohexen-1-yl)carbamate of melting point 89°–91° C. are obtained.

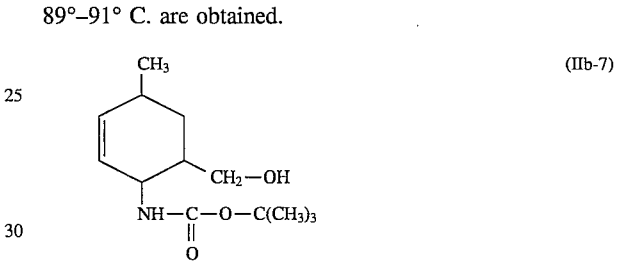
(IIb-7)

(Process B/d)

5 g (21 mmol) of tert-butyl (4-methyl-6-formyl -2-cyclohexen-1-yl)-carbamate are dissolved in 70 ml of tetrahydrofuran, and, after 1.6 g (42 mmol) of sodium borohydride have been added, the mixture is stirred for 15 minutes at 55° C. 17 ml of methanol are then slowly added dropwise at 55° C., and, when the addition is complete, stirring is continued for 3 hours at room temperature. Working-up is carried out under aqueous conditions, the mixture is extracted using diethyl ether, and, after drying over magnesium sulphate and evaporating, 4.8 g (95% of theory) of 2-[(tert-butyloxycarbonylamino) -5-methyl-3-cyclohexen-1-yl]-methanol is obtained as a white, waxy solid.

$^1$H-NMR$^{*)}$ (CDCl$_3$, 200 MHz): δ=1.00(d, 3H), 1.45(s, 9H), 1.75–2.40(m, 2H), 3.28–3.52 and 3.67–3.80 (m, 2H), 4.00–4.30 and 4.45–4.75 (m, 2H), 5.43–5.51 and 5.63–5.78 (m, 2H).

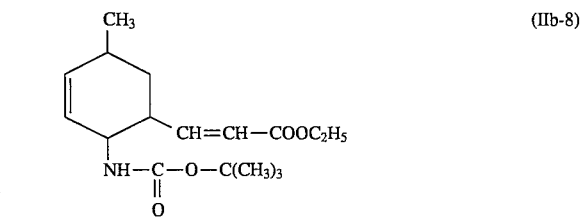
(IIb-8)

(Process B/e)

24 g (0.105 mol) of triethyl phosphonoacetate are added dropwise at 0° C. to a suspension of 3.4 g (80% strength in oil=0.1 mol) of sodium hydride. When the evolution of hydrogen has ceased, a solution of 25 g (0.105 mol) of tert-butyl (4-methyl-6-formyl-2-cyclohexen-1-yl)-carbamate in 30 ml of tetrahydrofuran is added dropwise. After the reaction mixture has been stirred for 4 hours at room temperature, it is added to 500 ml of water, and the mixture is extracted several times using ethyl acetate. The combined organic phases are washed with water and saturated sodium chloride solution and dried and concentrated. After purification by column chromatography on silica gel using the eluent petroleum ether/ethyl acetate (5:1), 26 g (80% of theory) of ethyl trans-(2-N-tert-butoxycarbonylamino-4-methyl-cyclohex-2-en)-1-yl)-acrylate are obtained.

$^{1}$H-NMR$^{*)}$ (CDCl$_3$, 200 MHz): δ=1.05(d, 3H), 1.20–1.35 (m, 3H), 1.43(s, 9H), 1.60–2.60(m, 4H), 4.15(q, 2H), 4.25–4.60(br.m, 2H), 5.50–5.95(m, 3H), 6.86–7.10 (m, 1H).

$^{*)}$ The $^{1}$H-NMR spectra were recorded in deuterochloroform (CDCl$_3$) with tetramethylsilane (TMS) as the internal standard. The chemical shift is indicated as δ value in ppm.

The precursors of the formula (IIb)

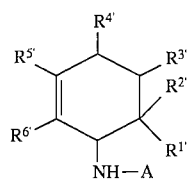

(IIb)

which are listed in Table 2 below are obtained analogously to the methods described in Examples (IIb-1) to (IIb-8) and following the instructions in the descriptions of the processes according to the invention:

TABLE 2

| Ex. No. | A | $R^1$ | $R^2$ | $R^3$ | $R^4$ | $R^5$ | $R^6$ | Physical constants |
|---|---|---|---|---|---|---|---|---|
| IIb-9 | $-\underset{\parallel}{C}-OC(CH_3)_3$ | H | —COOH | H | H | H | H | m.p.: 110–118° C. |
| IIb-10 | $-\underset{\parallel}{C}-OC(CH_3)_3$ | H | —COOH | H | $CH_3$ | H | H | m.p.: 194–196° C. |
| IIb-11 | $-\underset{\parallel}{C}-OC(CH_3)_3$ | H | —COOCH₃ | H | H | H | H | ¹H-NMR*)(CDCl₃, 200 MHz) δ = 1.42(9H), 1.70–2.10(4H), 2.73–2.85(1H), 3.68(3H), 4.48–4.59(1H), 4.85–4.95(1H), 5.60–5.86(2H) |
| IIb-12 | $-\underset{\parallel}{C}-OC(CH_3)_3$ | H | —COOCH₃ | H | C₆H₅ | H | H | ¹H-NMR*)(CDCl₃, 200 MHz) δ = 1.44(9H), 1.58–1.78(1H), 2.08–2.20(1H), 3.30–3.40(1H), 3.62(3H), 4.60–4.80(2H), 6.90(2H), 7.12–7.35(5H) |
| IIb-13 | $-\underset{\parallel}{C}-OC(CH_3)_3$ | H | —COOCH₃ | H | H | —CH₂—(CH₂)₂—CH₂— | H | ¹H-NMR*)(CDCl₃, 200 MHz) δ = 0.80–2.30(20H), 2.60–2.71(1H) 3.65(3H), 4.50(2H), 5.43(1H) |
| IIb-14 | $-\underset{\parallel}{C}-OC(CH_3)_3$ | H | —COOH | H | H | —CH₂—(CH₂)₂—CH₂— | H | m.p.: 160–168° C. |
| IIb-15 | $-\underset{\parallel}{C}-OC(CH_3)_3$ | $CH_3$ | —COOCH₃ | H | H | H | H | ¹H-NMR*)(CDCl₃, 200 MHz) δ = 1.18(3H), 1.44(9H), 3.68(3H), 5.50–5.80(2H) |
| IIb-16 | $-\underset{\parallel}{C}-OC(CH_3)_3$ | H | —CONH₂ | H | $CH_3$ | H | H | m.p.: 148–150° C. |
| IIb-17 | $-\underset{\parallel}{C}-OC(CH_3)_3$ | H | —COOCH₃ | H | $C_3H_7$ | H | H | ¹H-NMR*)(CDCl₃, 200 MHz) δ = 0.90(3H), 1.20–1.48(9H), 1.85–2.12(2H), 3.67(3H), 4.52(2H), 5.71(2H) |
| IIb-18 | $-\underset{\parallel}{C}-OC(CH_3)_3$ | H | —COOCH₃ | H | $C_2H_5$ | H | H | m.p.: 79–85° C. |
| IIb-19 | $-\underset{\parallel}{C}-OC(CH_3)_3$ | H | —COOH | H | $C_2H_5$ | H | H | m.p.: 149–167° C. |
| IIb-20 | $-\underset{\parallel}{C}-OC(CH_3)_3$ | H | —COOH | H | H | n-$C_4H_9$ | H | ¹H-NMR*)(CDCl₃, 200 MHz) δ = 0.89(3H), 1.10–1.50 and 1.80–2.00(20H), 2.70–2.85(1H), 4.40–4.60 and 5.00–5.20(1H) 5.35(2H) |

TABLE 2-continued

| Ex. No. | A | $R^{1'}$ | $R^2$ | $R^3$ | $R^{4'}$ | $R^{5'}$ | $R^6$ | Physical constants |
|---|---|---|---|---|---|---|---|---|
| IIb-21 | $-\underset{\overset{\|}{O}}{C}-OC(CH_3)_3$ | H | —COOH | H | H | $C_2H_5$ | H | m.p.: 120–128° C. (hygroscopic) |
| IIb-22 | $-\underset{\overset{\|}{O}}{C}-OC(CH_3)_3$ | H | —COOCH$_3$ | H | H | $C_2H_5$ | H | m.p.: 65–71° C. |
| IIb-23 | $-\underset{\overset{\|}{O}}{C}-OC(CH_3)_3$ | H | —COOH | H | $C_3H_7$ | H | H | m.p.: 116–142° C. |
| IIb-24 | $-\underset{\overset{\|}{O}}{C}-OC(CH_3)_3$ | H | —CN | H | $C_2H_5$ | H | H | m.p.: 121–122° C. |
| IIb-25 | $-\underset{\overset{\|}{O}}{C}-OC(CH_3)_3$ | H | —CN | H | CH$_3$ | H | H | MS: 183 M$^+$ (12), 153, 127, 83, 57(100) |
| IIb-26 | $-\underset{\overset{\|}{O}}{C}-OC(CH_3)_3$ | Cl | —CN | H | CH$_3$ | H | H | m.p.: 116–121° C. |
| IIb-27 | $-\underset{\overset{\|}{O}}{C}-OC(CH_3)_3$ | H | —NO$_2$ | —COOC$_2$H$_5$ | H | H | H | m.p.: 95–96° C. |
| IIb-28 | $-\underset{\overset{\|}{O}}{C}-OC(CH_3)_3$ | H | —NO$_2$ | 3-NO$_2$-C$_6$H$_4$ | CH$_3$ | H | H | m.p.: 180–185° C. |
| IIb-29 | $-\underset{\overset{\|}{O}}{C}-OCH_2-C_6H_5$ | H | —NO$_2$ | —COOC$_2$H$_5$ | CH$_3$ | H | H | m.p.: 88–91° C. |
| IIb-30 | $-\underset{\overset{\|}{O}}{C}-O-CH_3$ | H | —NO$_2$ | —COO—C$_4$H$_9$-t | CH$_3$ | H | H | m.p.: 178–181° C. |
| IIb-31 | $-\underset{\overset{\|}{O}}{C}-OC(CH_3)_3$ | H | —NO$_2$ | 2,6-Cl$_2$-C$_6$H$_3$ | CH$_3$ | H | H | m.p.: 180–183° C. |

TABLE 2-continued

| Ex. No. | A | R1' | R2 | R3 | R4' | R5 | R6' | Physical constants |
|---|---|---|---|---|---|---|---|---|
| IIb-32 | —C(=O)—OC(CH$_3$)$_3$ | H | —NO$_2$ | 3-NO$_2$-C$_6$H$_4$— | C$_2$H$_5$ | H | H | m.p.: 168–174° C. |
| IIb-33 | —C(=O)—OC(CH$_3$)$_3$ | H | —NO$_2$ | 2-Cl-3-NO$_2$-C$_6$H$_3$— | CH$_3$ | H | H | m.p.: 171–176° C. |
| IIb-34 | —C(=O)—OC(CH$_3$)$_3$ | H | —NO$_2$ | 3-NO$_2$-C$_6$H$_4$— | H | C$_4$H$_9$-n | H | m.p.: 205–206° C. |
| IIb-35 | —C(=O)—OC(CH$_3$)$_3$ | H | —NO$_2$ | 4-NO$_2$-C$_6$H$_4$— | CH$_3$ | H | H |  |
| IIb-36 | —C(=O)—OC(CH$_3$)$_3$ | H | —NO$_2$ | 2-NO$_2$-C$_6$H$_4$— | CH$_3$ | H | H | m.p.: 145–146° C. |
| IIb-37 | —C(=O)—OC(CH$_3$)$_3$ | H | —NO$_2$ | —COOC$_2$H$_5$ | —CH$_2$—(CH$_2$)$_2$—CH$_2$— | | H | MS: 368 M$^+$ (0.1), 57(100) |
| IIb-38 | —C(=O)—OCH$_2$—CH=CH$_2$ | H | —NO$_2$ | —COOC$_4$H$_9$-t | H | H | H | m.p.: 123–124° C. |
| IIb-39 | —C(=O)—OCH$_2$—CH=CH$_2$ | H | —NO$_2$ | —COOC$_4$H$_9$-t | CH$_3$ | H | H | m.p.: 120–126° C. |

TABLE 2-continued
| Ex. No. | A | R¹' | R² | R³ | R⁴' | R⁵' | R⁶' | Physical constants |
|---|---|---|---|---|---|---|---|---|
| IIb-40 | —C—OC(CH₃)₃<br>‖<br>O | H | | 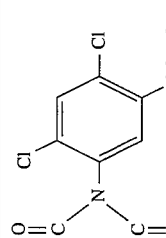 | CH₃ | H | H | m.p.: 186–191° C. |
| IIb-41 | —C—OC(CH₃)₃<br>‖<br>O | H | |  | 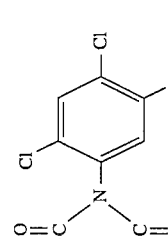 | H | H | m.p.: 204–205° C. |
| IIb-42 | —C—OC(CH₃)₃<br>‖<br>O | H | |  | 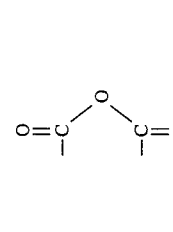 | H | H | m.p.: 182–184° C. |
| IIb-43 | —C—OC(CH₃)₃<br>‖<br>O | H | |  | H | H | H | m.p.: 88–93° C. |
| IIb-44 | —C—OC(CH₃)₃<br>‖<br>O | H | | 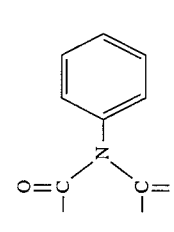 |  | H | H | m.p.: 45–51° C. |

TABLE 2-continued

| Ex. No. | A | R¹' | R²' | R³' | R⁴' | R⁵' | R⁶' | Physical constants |
|---|---|---|---|---|---|---|---|---|
| IIb-45 | —C(=O)—OC(CH₃)₃ | H | 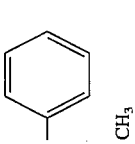 | | CH₃ | H | H | m.p.: 132–135° C. |
| IIb-46 | —C(=O)—OC(CH₃)₃ | H | —NO₂ | —COO—C₄H₉-t |  | H | H | m.p.: 197–199° C. |
| IIb-47 | —C(=O)—OC(CH₃)₃ | H | NO₂ |  | CH₃ | H | H | m.p.: 165–168° C. |
| IIb-48 | —C(=O)—OC(CH₃)₃ | H | NO₂ | 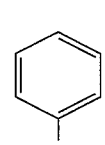 | CH₃ | H | H | m.p.: 168–172° C. |
| IIb-49 | —C(=O)—OC(CH₃)₃ | H | NO₂ | —COOC₂H₅ | | H | H | m.p.: 130–135° C. |
| IIb-50 | —C(=O)—OC(CH₃)₃ | H | NO₂ | —COO—C₄H₉-t | CH₃ | H | H | m.p.: 180–185° C. |
| IIb-51 | —C(=O)—OC(CH₃)₃ | H | NO₂ | —COO—C₄H₉-t | H | H | H | m.p.: 165–168° C. |
| IIb-52 | —C(=O)—OC(CH₃)₃ | H | CHO | CH₃ | H | H | H | ¹H-NMR*)(CDCl₃, 200 MHz) $\delta$ = 0.95–1.25(4 isomers, 3H), 1.42(s,9H), 5.55–5.90(m,2H), 9.60–9.85(4 isomers, 1H) |
| IIb-53 | —C(=O)—OC(CH₃)₃ | H | CHO | H | H | H | H | IR (CH₂Cl₂): 3300, 2950, 2710, 1700 cm⁻¹ |
| IIb-54 | —C(=O)—OC(CH₃)₃ | H | CHO | H | CH₃ | H | H | IR (CH₂Cl₂): 3400, 2950, 2860, 1720 cm⁻¹ |

TABLE 2-continued

| Ex. No. | A | R¹' | R² | R³ | R⁴' | R⁵' | R⁶' | Physical constants |
|---|---|---|---|---|---|---|---|---|
| IIb-55 | $-\underset{\underset{O}{\|\|}}{C}-OC(CH_3)_3$ | F | CHO | H | $CH_3$ | H | H | MS: 201 [M⁺-isobutene](5), 183, 153, 127, 83, 57 |
| IIb-56 | $-\underset{\underset{O}{\|\|}}{C}-OC(CH_3)_3$ | H | $-CH=CH-COOH$ | H | $CH_3$ | H | H | m.p.: 106–136° C. |
| IIb-57 | $-\underset{\underset{O}{\|\|}}{C}-OC(CH_3)_3$ | H | $-CH=CH-COOH$ | H | H | H | H | m.p.: 107–130° C. |
| IIb-58 | $-\underset{\underset{O}{\|\|}}{C}-OC(CH_3)_3$ | H | $-CH=CH-COOC_2H_5$ | H | H | H | H | m.p.: 59–65° C. |
| IIb-59 | $-\underset{\underset{O}{\|\|}}{C}-OC(CH_3)_3$ | H | $-CH_2OH$ | H | H | H | H | ¹H-NMR*)(CDCl₃, 200 MHz) δ = 1.45(9H), 1.65–2.13(4H), 3.30–3.75(2H), 4.08–4.30(1H), 4.78–4.98(1H), 5.45–5.93(2H) |
| IIb-60 | $-\underset{\underset{O}{\|\|}}{C}-OC(CH_3)_3$ | H | | 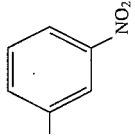 | H | H | H | m.p.: 83° C. |
| IIb-61 | $-\underset{\underset{O}{\|\|}}{C}-OC(CH_3)_3$ | H | $NO_2$ | 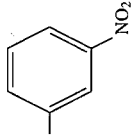 | H | $-CH(CH_3)_2$ | H | m.p.: 166–170° C. |
| IIb-62 | $-\underset{\underset{O}{\|\|}}{C}-OC(CH_3)_3$ | H | COOH | H | H | $-CH(CH_3)_2$ | H | m.p.: 100–124° C. |
| IIb-63 | $-\underset{\underset{O}{\|\|}}{C}-OC(CH_3)_3$ | H | $COOCH_3$ | H | H | $-CH(CH_3)_2$ | H | m.p.: 85–93° C. |
| IIb-64 | $-\underset{\underset{O}{\|\|}}{C}-OC(CH_3)_3$ | H | $NO_2$ | H | $C_3H_7$ | H | H | m.p.: 167–181° C. |

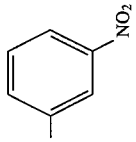

TABLE 2-continued

| Ex. No. | A | R1' | R2' | R3' | R4' | R5' | R6' | Physical constants |
|---|---|---|---|---|---|---|---|---|
| IIb-74 | —C(=O)—CH3 | H | —CO2H | H | CH3 | H | H | m.p.: 202–220° C. |
| IIb-75 | —C(=O)—(CH2)5CH3 | H | —CO2H | H | CH3 | H | H | m.p.: 144–146° C. |
| IIb-76 | —C(=O)—(CH2)16CH3 | H | —CO2H | H | CH3 | H | H | m.p.: 107° C. |
| IIb-77 | —C(=O)—OC(CH3)3 | H | —CO2CH2CH(CH3)2 | H | CH3 | H | H | m.p.: 63–64° C. |
| IIb-78 | —C(=O)—OC(CH3)3 | H | —CO2CH3 | H | CH(CH3)2 | H | H | 1H-NMR (CDCl3): δ = 0.90(6H); 1.43(9H); 3.68(3H); 5.75(2H). |
| IIb-79 | —C(=O)—OC(CH3)3 | H | —CO2CH3 | H | CH3 | CH3 | H | 1H-NMR (CDCl3): δ = 1.05(3H); 1.40(9H); 1.68(3H); 3.67(3H); 5.45(1H). |
| IIb-80 | —C(=O)—OC(CH3)3 | H | —CO2CH3 | H | CH2CH(CH3)2 | 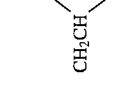 | H | 1H-NMR (CDCl3): δ = 0.73–0.86(8H); 1.43(9H); 3.68(3H); 5.82(1H); 7.15–7.30(5H). |
| IIb-81 | —C(=O)—OC(CH3)3 | H | —CO2H | 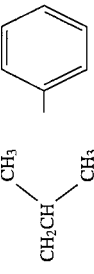 | CH(CH3)2 | H | H | m.p.: 154–158° C. |
| IIb-82 | —C(=O)—OC(CH3)3 | H | —CO2H | H | CH3 |  | H | m.p.: 147–152° C. |
| IIb-83 | —C(=O)—OC(CH3)3 | H | —CO2H | H | CH2CH(CH3)2 | CH3 | H | m.p.: 122–125° C. |
| IIb-84 | —C(=O)—OC(CH3)3 | H | —NO2 | H | CH3 | H | H | m.p.: 169–170° C. |

TABLE 2-continued

| Ex. No. | A | R¹' | R²' | R³' | R⁴' | R⁵' | R⁶' | Physical constants |
|---|---|---|---|---|---|---|---|---|
| IIb-85 | -C(=O)-OC(CH₃)₃ | H | -CN | H | CH₂CH(CH₃)₂ | CH(CH₃)₂ | H | m.p.: 117-121° C. |
| IIb-86 | -C(=O)-OC(CH₃)₃ | H | -CN | H | CH(CH₃)₂ | C₆H₅ | H | m.p.: 84-105° C. |
| IIb-87 | -C(=O)-OC(CH₃)₃ | H | -CO₂H | H | CH(CH₃)₂ | C₆H₅ | H | m.p.: 151-171° C. (Z) |
| IIb-88 | -C(=O)-OC(CH₃)₃ | H | -CO₂H | H | CH₂CH(CH₃)₂ | CH(CH₃)₂ | H | m.p.: 150-156° C. |
| IIb-89 | -C(=O)-OC(CH₃)₃ | H | -CO₂H | H |  | H | H | MS: 307 [M⁺] |

*) The ¹H-NMR spectra were recorded in deuterochloroform (CDCl₃) with tetramethylsilane (TMS) as the internal standard. The chemical shift is indicated as δ value in ppm.

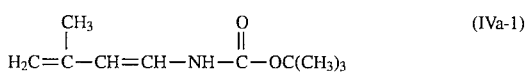

A solution of 54 g (0.5 mol) of ethyl chloroformate in 150 ml of acetone is added at –5° C. in the course of 30 minutes to a solution of 56 g (0.5 mol) of trans-4-methyl-2,4-pentadienecarboxylic acid and 80 g (0.62 mol) of N,N-diisopropyl ethylamine in 300 ml of acetone. After the mixture had remained at 0° C. for 30 more minutes, an ice-cooled solution of 65 g (1 mol) of sodium azide in 150 ml of water is added dropwise. The mixture is stirred at 0° C. for 15 minutes and then worked up using water/toluene. The toluene phase, which has been concentrated to about 300 ml, is then added dropwise to a solution, boiling under reflux, of 29.6 g (0.4 mol) of tert-butanol and 250 mg (1.5 mmol) of tert-butylcatechol in 200 ml of toluene. The course of the reaction is monitored by IR spectroscopy. The mixture is allowed to cool to room temperature and concentrated. After separation by column chromatography using the eluent petroleum ether/ethyl acetate (6:1), 59 g (65% of theory) of tert-butyl trans-3-methyl-1,3-butadiene-1-carbamate are obtained.

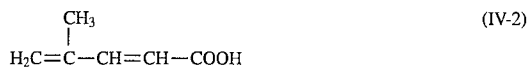

2.5 g (0.1 mol) of lithium hydroxide are added at 0° C. to 10 g (0.07 mol) of ethyl trans-4-methyl-2,4-pentadienecarboxylate, dissolved in a solvent mixture of 75 ml of methanol, 17 ml of tetrahydrofuran and 2.5 ml of water, and the mixture is stirred for 20 hours at room temperature. After the mixture has been diluted with 200 ml of water, it is extracted once using diethyl ether, and a pH of 1 is established in the aqueous phase at 0° C. using concentrated hydrochloric acid. The mixture is extracted using diethyl ether, the combined organic phases are washed several times with water and saturated sodium chloride solution, and, after drying and concentrating, 6.1 g (76% of theory) of trans-4-methyl-2,4-pentadienecarboxylic acid are obtained.

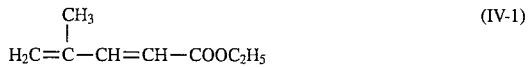

77 g (2.57 mol) of sodium hydride (80% strength in oil) are added in portions at 0° C. under a nitrogen atmosphere to a solution of 630 g (2.8 mol) of triethyl phosphonoacetate in 500 ml of tetrahydrofuran. The cold bath is removed, and stirring is continued until the evolution of hydrogen has ceased (about 30 minutes). A solution of 200 g (2.8 mol) of methacrolein in 2000 ml of tetrahydrofuran is then added dropwise at 0° C., and stirring is continued for 1 hour at 0° C. and for 2 hours at room temperature. For working up, the batch is divided, water is added, and the mixture is extracted several times using ethyl acetate. After drying, concentrating and distilling, 146 g (37% of theory) of ethyl trans-4-methyl-2,4-pentadienecarboxylate of boiling point 76°–90° C./20 bar are obtained.

USE EXAMPLES

In the following use examples, the compound listed below is employed as comparison substance:

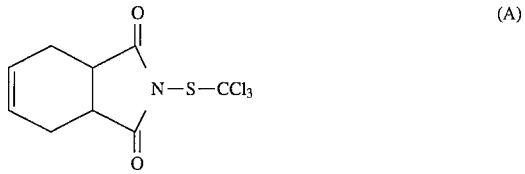

cis-N-[(trichloromethyl)thio]-4-cyclohexene-1,2-dicarboximide (disclosed in Science, (Washington) 115, 84 (1952); U.S. Pat. No. 2,553,770).

EXAMPLE A

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example the compound (I-3) according to the invention shows a better activity than comparison substance (A).

TABLE A

| | Venturia test (apple)/protective |
|---|---|
| Active compound | Degree of effectiveness in % of the untreated control at an active compound concentration of 5 ppm |
| (structure A shown)<br>(known)    (A) | 57 |
| (structure I-3 shown)<br>(I-3) | 74 |

EXAMPLE B

Phytophthora test (tomato)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqaeous spore suspension of Phytophthora infestans.

The plants are then placed in an incubation cabin at about 20° C. and a relative atmospheric humidity of 100%.

Evaluation is carried out 3 days after the inoculation.

In this test, for example the substances (I-3) and (I-4) according to the invention show a very high degree of effectiveness at an active compound concentration of 10 ppm.

TABLE B

| Phytophthora test (tomato)/protective/curative/systemic | |
|---|---|
| Active compound | Degree of effectiveness in % of the untreated control at an active compound concentration of 10 ppm |
| (I-3) | 78 |
| (I-4) | 89 |

EXAMPLE C

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% =no action (like untreated control)
100% =total destruction In this test, for example the compound (I-4) shows a very good herbicidal action, in particular in wheat.

TABLE C

| | Post-emergence greenhouse | | | | | | | |
|---|---|---|---|---|---|---|---|---|
| Active compound | Application rate in g/ha | | | Wheat | | | | |
| 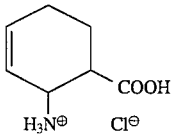 (I-4) | 500 | 0 | 100 | 100 | 100 | 90 | 95 | 100 | 95 |

It will be appreciated that the instant specification and claims are set forth by way of illustration and not limitation, and that various modifications and changes may be made without departing from the spirit and scope of the present invention.

What is claimed is:

1. A substituted 2-cyclohexen-1-yl-amine derivative of the formula

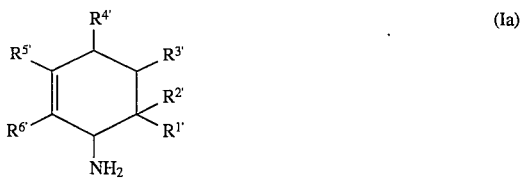

(Ia)

in which $R^{1'}$ represents hydrogen, alkyl or halogen, $R^{2'}$ represents formyl, or

$R^{3'}$, $R^{4'}$, $R^{5'}$ and $R^{6'}$ are identical or different in each case represent hydrogen, alkyl, alkoxy or represent unsubstituted or substituted aryl, $R^{8'}$ represents hydroxyl, hydroxyalkyloxy, halogenalkyloxy, alkoxy or alkoxyalkyloxy, unsubstituted or substituted cycloalkyloxy, unsubstituted or substituted aralkyloxy, unsubstituted or substituted aryloxy, unsubstituted or substituted aralkyl, alkylthio or unsubstituted or substituted arylthio, or represents a group

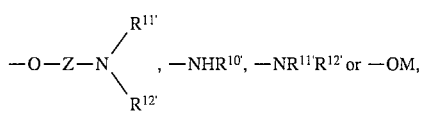

$R^{10'}$ represents hydrogen, alkyl or unsubstituted or substituted aryl, $R^{11'}$ and $R^{12'}$ are identical or different and in each case represent alkyl or unsubstituted or substituted aryl, M represents an equivalent of a corresponding alkali metal cation, alkaline earth metal cation or ammonium cation and Z represents a non-branched or branched alkyl chain, $R^{4'}$ and $R^{5'}$ together represents an alkyl chain which has 3 or 4 carbon atoms and which is linked via the 4- and 3-positions, or an addition product thereof with an acid or metal salt, with the exception of the cis-diastereomer of compounds of the formula

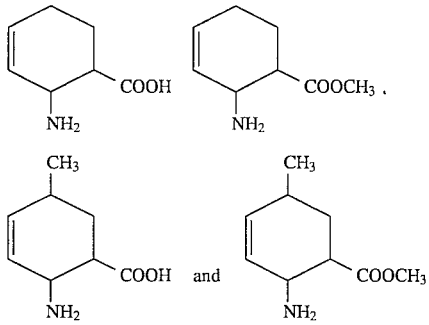

or forms a complex with a compound of the formula

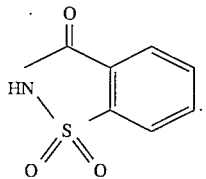

2. A substituted 2-cyclohexen-1-yl-amine derivative according to claim 1, in which $R^{1'}$ represents hydrogen, straight-chain or branched alkyl having 1 to 6 carbon atoms, or fluorine, chlorine or bromine, $R^{3'}$, $R^{4'}$, $R^{5'}$ and $R^{6'}$ are identical or different and in each case represent hydrogen, in each case straight-chain or branched alkyl alkoxy having 1 to 8 carbon atoms, in each case having 2 to 8 carbon atoms, or alkoxyalkyloxy, in each case having 1 to 8 carbon atoms in the individual alkyl moieties, or represents aryl having 6 to 10 carbon atoms in the aryl moiety and being unsubstituted or monosubstituted to pentasubstituted by identical or different substituents selected from the group consisting of halogen, nitro, cyano, amino, $C_1$–$C_4$-alkyl, $C_1$–$C_4$-alkoxy, $C_1$–$C_4$-alkylthio, halogeno-($C_1$–$C_4$)-alkyl, halogeno-($C_1$–$C_4$)-alkoxy, halogeno-($C_1$–$C_4$)-alkylthio, each having 1 to 9 identical or different halogen atoms, and di-($C_1$–$C_4$)-alkylamino, $R^{8'}$ represents hydroxyl, straight-chain or branched hydroxyalkyloxy with 1 to 8 carbon atoms, straight-chain or branched halogenalkyloxy with 1 to 8 carbon atoms an 1 to 17 identical or different halogen atoms, cycloalkyloxy with 3 to 6 carbon atoms which is unsubstituted or mono or polysubstituted by identical or different halogen atoms, in each case straight-chain or branched alkoxy or alkylthio having 1 to 6 carbon atoms, or straight-chain or branched alkoxyalkyloxy, in each case having 1 to 6 carbon atoms in the alkoxy moiety or alkyl moiety, or aryloxy, arylthio, aralkyl or aralkyloxy, in each case having 6 to 10 carbon atoms in the aryl moiety and where appropriate 1 to 8 carbon atoms in the alkyl moiety, and in each case being unsubstituted or monosubstituted to pentasubstituted on the aryl moiety by identical or different substituents as set forth for aryl hereinabove, or represents a group

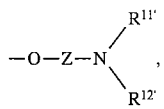

$-NH^{10'}$, $-NR^{11'}R^{12'}$ or $-OM$, $R^{10'}$ represents hydrogen, straight-chain or branched alkyl having 1 to 6 carbon atoms, or aryl which has 6 to 10 carbon atoms and which is unsubstituted or monosubstituted to pentasubstituted by identical or different substituents as set forth for aryl hereinabove, $R^{11'}$ represents straight-chain or branched alkyl having 1 to 6 carbon-atoms, or aryl which has 6 to 10 carbon atoms and which is unsubstituted or monosubstituted to pentasubstituted by identical or different substituents as set forth for aryl hereinabove, $R^{12'}$ represents straight-chain or branched alkyl having 1 to 6 carbon atoms, or aryl which has 6 to 10 carbon atoms and which is unsubstituted or monosubstituted to pentasubstituted by identical or different substituents as set forth for aryl hereinabove, M represents hydrogen, or represents an equivalent of a corresponding alkali metal cation, alkaline earth metal cation or ammonium cation and Z represents a non-branched or branched alkyl chain with 1 to 8 carbon atoms or $R^{4'}$ and $R^{5'}$ together represents an alkyl chain which has 3 or 4 carbon atoms and which is linked via the 4- and 3-positions, or an addition product thereof with an acid or metal salt.

3. A substituted 2-cyclohexen-1-yl-amine derivative according to claim 1, in which $R^{1'}$ represents hydrogen, straight-chain or branched alkyl having 1 to 4 carbon atoms, or-fluorine, chlorine or bromine, $R^{3'}$, $R^{4'}$, $R^{5'}$ and $R^{6'}$ are identical or different and in each case represent hydrogen, in each case straight-chain or branched alkyl or alkoxy having 1 to 6 carbon atoms, or alkoxyalkyloxy, in each case having 1 to 6 carbon atoms in the individual alkyl moieties, or represent phenyl unsubstituted or monosubstituted to trisubstituted by identical or different substituents selected from the group consisting of fluorine, chlorine, bromine, nitro, cyano, amino, $C_1$–$C_2$-alkyl, $C_1$–$C_3$-alkoxy, $C_1$–$C_2$-alkylthio, halogeno-($C_1$–$C_2$)-alkyl, halogeno-($C_1$–$C_2$)-alkoxy, and halogeno-($C_1$–$C_2$)-alkylthio, in each case having 1 to 5 identical or different fluorine and/or chlorine atoms, and di-($C_1$–$C_2$)-alkylamino, $R^{8'}$ represents, straight-chain or branched hydroxyalkyloxy with 1 to 6 carbon atoms, straight-chain or branched halogenalkyloxy with 1 to 6 carbon atoms and 1 to 13 identical or different halogen atoms which is unsubstituted cycloalkyloxy with 3 to 6 carbon atoms which is unsubstituted or mono or trisubstituted by identical or different fluoro, chloro or bromo atoms, or alkylthio having 1 to 4 carbon atoms, or straight-chain or branched alkoxyalkyl-alkoxy, in each case having 1 to 4 carbon atoms in the alkoxy moiety or alkyl moiety, or phenyloxy, phenylthio or phenylalkyloxy, where appropriate in each case having 1 to 6 carbon atoms in the alkyl moiety, and in each case unsubstituted or monosubstituted to trisubstituted in the phenyl moiety by identical or different substituents as set forth for phenyl hereinabove, or represents a group

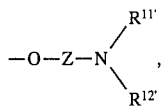

$-NHR^{10'}$, $-NR^{11'}R^{12'}$ or $-OM$, $R^{10'}$ represents hydrogen, straight-chain or branched alkyl having 1 to 4 carbon atoms, or phenyl which is unsubstituted or monosubstituted to trisubstituted by identical or different substituents, as set forth for phenyl hereinabove, $R^{11'}$ represents straight-chain or branched alkyl having 1 to 4 carbon atoms, or phenyl which is unsubstituted or monosubstituted to trisubstituted by identical or different substituents as set forth for phenyl hereinabove, $R^{12'}$ represents straight-chain or branched alkyl having 1 to 4 carbon atoms, or phenyl which is unsubstituted or monosubstituted to trisubstituted by identical or different substituents as set forth for phenyl hereinabove, M represents hydrogen, or represents an equivalent of a corresponding alkali metal cation, alkaline earth metal cation or ammonium cation and Z represents a non-branched or branched alkyl chain with 1 to 6 carbon atoms or $R^{4'}$ and $R^{5'}$ together represent an alkyl chain which has 3 or 4 carbon atoms and which is linked via the 4- and 3-positions, or an addition product thereof with an acid or metal salt.

4. A substituted 2-cyclohexen-1-yl-amine derivative according to claim 2, in which $R^{1'}$ represents hydrogen, straight-chain or branched alkyl having 1 to 4 carbon atoms, or fluorine, chlorine or bromine, $R^{3'}$, $R^{4'}$, $R^{5'}$ and $R^{6'}$ are identical or different and in each case represent hydrogen, in each case straight-chain or branched alkyl or alkoxy having 1 to 6 carbon atoms, in each case straight-chain or branched alkenyl, alkinyl, alkenyloxy or alkinyloxy, in each case having 2 to 6 carbon atoms, or alkoxyalkyloxy, in each case having 1 to 6 carbon atoms in the individual alkyl moieties, or represent phenyl unsubstituted or monosubstituted to trisubstituted in the phenyl moiety by identical or different substituents selected from the group consisting of fluorine, chlorine, bromine, nitro, cyano, amino, $C_1$–$C_2$-alkyl, $C_1$–$C_3$-alkoxy, $C_1$–$C_2$-alkylthio, halogeno-$(C_1$–$C_2)$-alkyl, halogeno-$(C_1$–$C_2)$-alkoxy, and halogeno-$(C_1$–$C_2)$-alkylthio, in each case having 1 to 5 identical or different fluorine and/or chlorine atoms, and di-$(C_1$–$C_2)$-alkylamino, $R^{8}$ represents, straight-chain or branched hydroxyalkyloxy with 1 to 6 carbon atoms, straight-chain or branched halogenalkyloxy with 1 to 6 carbon atoms and 1 to 13 identical or different halogen atoms which is unsubstituted cycloalkyloxy with 3 to 6 carbon atoms which is unsubstituted or mono or trisubstituted by identical or different fluoro, chloro or bromo atoms, or alkylthio having 1 to 4 carbon atoms, or straight-chain or branched alkoxyalkyl-alkoxy, in each case having 1 to 4 carbon atoms in the alkoxy moiety or alkyl moiety, or phenyloxy, phenylthio or phenylalkyloxy, where appropriate in each case having 1 to 6 carbon atoms in the alkyl moiety, and in each case unsubstituted or monosubstituted to trisubstituted in the phenyl moiety by identical or different substituents as set forth for phenyl hereinabove, or represents a group

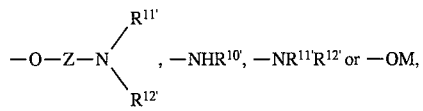

$R^{10'}$ represents hydrogen, straight-chain or branched alkyl having 1 to 4 carbon atoms, or phenyl which is unsubstituted or monosubstituted to trisubstituted by identical or different substituents, the phenyl substituents being the phenyl substituents mentioned above, $R^{11'}$ represents straight-chain or branched alkyl having 1 to 4 carbon atoms, or phenyl which is unsubstituted or monosubstituted to trisubstituted by identical or different substituents, the phenyl substituents being the phenyl substituents mentioned above, $R^{12'}$ represents straight-chain or branched alkyl having 1 to 4 carbon atoms, or phenyl which is unsubstituted or monosubstituted to trisubstituted by identical or different substituents, the phenyl substituents being the phenyl substituents mentioned above, M represents hydrogen, or represents an equivalent of a corresponding alkali metal cation, alkaline earth metal cation of ammonium cation, and represents a non-branched or branched alkyl chain with 1 to 6 carbon atoms, or $R^{4'}$ and $R^{5'}$ together represent an alkyl chain which has 3 or 4 carbon atoms and which is linked via the 4- and 3-positions.

5. A compound according to claim 1, of the formula

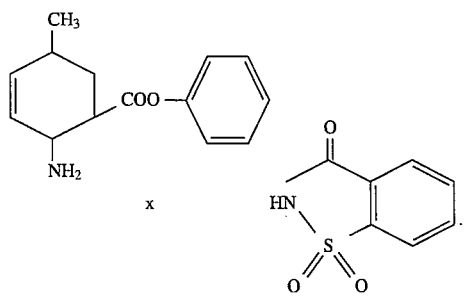

6. A pesticidal composition comprising a pesticidally effective amount of a compound or addition product thereof according to claim 1 and a diluent.

7. A method of combating pests which comprises applying to such pests or to a pest habitat a pesticidally effective amount of a compound or addition product thereof according to claim 1.

* * * * *

UNITED STATES PATENT AND TRADEMARK OFFICE
CERTIFICATE OF CORRECTION

PATENT NO. : 5,622,916
DATED : April 22, 1997
INVENTOR(S) : Kunisch, et al.

It is certified that error appears in the above-indentified patent and that said Letters Patent is hereby corrected as shown below:

Col. 73, line 35   Delete " $R^{40'}$ and substitute -- $R^{4'}$ --

Col. 74, line 36   Before " represents " insert -- Z --

Signed and Sealed this

Twenty-sixth Day of August, 1997

Attest:

Attesting Officer

BRUCE LEHMAN

Commissioner of Patents and Trademarks